(12) United States Patent
Schöning et al.

(10) Patent No.: US 8,471,031 B2
(45) Date of Patent: *Jun. 25, 2013

(54) PROCESS FOR THE PREPARATION OF STERICALLY HINDERED NITROXYL ETHERS

(75) Inventors: Kai-Uwe Schöning, Oberwil (CH); Walter Fischer, Reinach (CH); Abdel-Ilah Basbas, Basel (CH); Alexander Dichtl, Lörrach (DE)

(73) Assignee: BASF SE, Ludwigshafen (DE)

( * ) Notice: Subject to any disclaimer, the term of this patent is extended or adjusted under 35 U.S.C. 154(b) by 999 days.

This patent is subject to a terminal disclaimer.

(21) Appl. No.: 12/308,519

(22) PCT Filed: Jun. 25, 2007

(86) PCT No.: PCT/EP2007/056292
§ 371 (c)(1), (2), (4) Date: Dec. 17, 2008

(87) PCT Pub. No.: WO2008/003602
PCT Pub. Date: Jan. 10, 2008

(65) Prior Publication Data
US 2010/0249401 A1    Sep. 30, 2010

(30) Foreign Application Priority Data

Jul. 5, 2006 (EP) .................................... 06116619
Feb. 22, 2007 (EP) .................................... 07102895

(51) Int. Cl.
| C07D 211/94 | (2006.01) |
| C07D 401/12 | (2006.01) |
| C07D 401/14 | (2006.01) |
| C07D 403/12 | (2006.01) |
| C07D 403/14 | (2006.01) |
| C07B 43/00 | (2006.01) |
| C07B 41/00 | (2006.01) |

(52) U.S. Cl.
USPC ........... 546/184; 546/188; 546/189; 544/198; 544/209

(58) Field of Classification Search
USPC .................... 546/184, 188, 189; 544/19, 209, 544/198
See application file for complete search history.

(56) References Cited

U.S. PATENT DOCUMENTS

| 4,921,962 A | 5/1990 | Galbo et al. ............... 546/184 |
| 5,374,729 A | 12/1994 | Galbo ............................ 546/242 |
| 7,361,755 B2 * | 4/2008 | Pastor et al. ..................... 544/1 |
| 2003/0171461 A1 | 9/2003 | Hafner et al. ................... 524/99 |
| 2005/0104042 A1 | 5/2005 | Frey et al. ....................... 252/399 |
| 2007/0191516 A1 | 8/2007 | Frey et al. ....................... 524/99 |

FOREIGN PATENT DOCUMENTS

| EP | 0389419 | 9/1990 |
| GB | 2347928 | 9/2000 |
| WO | 2005/005388 | 1/2005 |

OTHER PUBLICATIONS

P. Carloni et al., J. Heterocyclic Chem., vol. 40, pp. 459-464, (May-Jun. 2003).
M. Ivan et al., Photochemistry and Photobiology, vol. 78, No. 4, (2003), pp. 416-419.
T. Inokuchi et al., Tetrahedron Letters, vol. 36, No. 18, (1995), pp. 3223-3226.
C. G. Johnson et al., Anal. Chem., vol. 68, (1996), pp. 867-872.
T. Ren et al., Bull. Chem. Soc. Jpn., vol. 69, (1996), pp. 2935-2941.
D. Barton et al., Tetrahedron, vol. 52, No. 31, (1996), pp. 10301-10312.
J. Babiarz et al., J. Org. Chem., vol. 67, (2002), pp. 6831-6834.

* cited by examiner

*Primary Examiner* — Venkataraman Balasubramanian
(74) *Attorney, Agent, or Firm* — Tyler A. Stevenson

(57) ABSTRACT

The present invention relates to a novel process for the preparation of a sterically hindered nitroxyl ether from the corresponding sterically hindered nitroxyl radical by reacting it with a carbonyl compound and a hydroperoxide. The compounds prepared by this process are effective stabilizers for polymers against harmful effects of light, oxygen and/or heat, as flame-retardants for polymers and as polymerization regulators.

13 Claims, No Drawings

PROCESS FOR THE PREPARATION OF STERICALLY HINDERED NITROXYL ETHERS

The present invention relates to a novel process for the preparation of a sterically hindered nitroxyl ether from the corresponding sterically hindered nitroxyl radical by reacting it with a carbonyl compound and a hydroperoxide. The compounds prepared by this process are effective as stabilizers for polymers against harmful effects of light, oxygen and/or heat, as flame-retardants for polymers, as rheology modifiers and as polymerization regulators.

The term sterically hindered nitroxyl radical used in the present invention is a synonym for the term sterically hindered nitroxide, which is also frequently used in the literature. Consequently the term sterically hindered nitroxyl ether used in the present invention is used as a synonym for sterically hindered nitroxide ether or sterically hindered alkoxyamine.

Since sterically hindered nitroxyl ethers are of considerable industrial interest, many attempts have been made to develop industrially applicable processes for their manufacture.

For example WO 01/92228 describes a process for the preparation of nitroxyl ethers, e.g. N-hydrocarbyloxy substituted hindered amine compounds, by the reaction of the corresponding N-oxyl intermediate with a hydrocarbon in the presence of an organic hydroperoxide and a copper catalyst.

WO 03/045919 describes a process for the preparation of nitroxyl ethers, e.g. N-hydrocarbyloxy substituted hindered amine compounds, by the reaction of the corresponding N-oxyl intermediate with a hydrocarbon in the presence of an organic hydroperoxide and an iodide catalyst.

Reactions of 2,2,6,6-tetramethyl-1-oxopiperidinium chloride with ketones bearing an α-H atom are for example described by T. Ren et al. in Bull. Chem. Soc. Jpn., 69, 2935-2941 (1996) and by Y.-C. Liu et al. in Chinese Journal of Chemistry, 14 (3), 252-258 (1996).

Surprisingly it has been found that sterically hindered nitroxyl ethers can be prepared by reacting a sterically hindered nitroxyl compound with a compound containing a carbonyl group, such as a ketone or an aldehyd in the presence of a hydroperoxide and a metal catalyst.

In many cases, very high yields are achieved in short reaction times. Additionally, the starting material concentration can be chosen very high, thus leading to an excellent volume time yield. Reaction conditions are mild as compared to other prior art processes and the reaction is very selective without concomitant formation of dimeric, trimeric or oligomeric by-products. Moreover the present process allows for the formation of sterically hindered nitroxyl ethers possessing defined alkoxide residues instead of a mixture of isomers as in other state of the art processes.

Furthermore the instant process allows the preparation of sterically hindered nitroxyl ethers, which can not be prepared, or only prepared with an insufficient yield with prior art processes.

One aspect of the invention is a process for the preparation of a sterically hindered nitroxyl ether which comprises reacting a corresponding sterically hindered nitroxyl radical with an alkyl radical, which is formed in the reaction of a ketone, aldehyde, diketone or dialdehyde oligoketone or oligoaldehyde with a hydroperoxide in the presence of a metal catalyst, with the proviso that, if the sterically hindered nitroxyl radical is 2,2,6,6-tetramethylpiperidine-1-oxyl (TEMPO), the ketone is not acetone.

The term alkyl radical, shall not be limited to a free radical but also comprises a transition state between the reacting components, wherein the electrons are separated.

In general the metal catalyst should be present in the reaction, in order to achieve the desired high yields. However, there are cases where the reaction can be carried out without the metal catalyst.

For instance the ketone, aldehyde, diketone or dialdehyde is of formula (Ia)

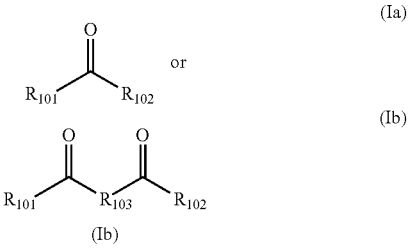

wherein $R_{101}$ and $R_{102}$ are independently hydrogen, straight or branched chain $C_1$-$C_{24}$alkyl, straight or branched chain $C_2$-$C_{18}$alkenyl, $C_2$-$C_{18}$alkinyl, $C_5$-$C_{12}$cycloalkyl, $C_5$-$C_{12}$cyclo-alkenyl, phenyl, naphthyl or $C_7$-$C_{15}$-phenylalkyl; or said straight or branched chain $C_1$-$C_{24}$ alkyl, straight or branched chain $C_2$-$C_{24}$ alkenyl, $C_5$-$C_{12}$cycloalkyl, $C_5$-$C_{12}$cycloalkenyl, $C_2$-$C_{18}$alkinyl can be substituted by one or more -halogen, —OH, —$OR_{122}$, —$NH_2$, —$NHR_{122}$, —$N(R_{122})_2$, —$NHCOR_{122}$, —$NR_{122}COR_{122}$, —$OCOR_{122}$, —$COR_{122}$, —$SO_2R_{122}$, —$SR_{122}$, —$SOR_{122}$, —$P(OR_{122})_3$, —$P(O)(OR_{122})_2$, $P(R_{122})_3$; or said straight or branched chain unsubstituted or substituted $C_1$-$C_{24}$ alkyl, straight or branched chain unsubstituted or substituted $C_2$-$C_{24}$ alkenyl, $C_5$-$C_{12}$ cycloalkyl, $C_5$-$C_{12}$cycloalkenyl or $C_2$-$C_{18}$ alkinyl can also be interrupted by one or more —O—, —NH— or —$NR_{122}$— groups or combinations thereof; or said phenyl, naphthyl or $C_7$-$C_{15}$-phenylalkyl can also be substituted by one or more halogen, —CN, —$CF_3$, —$NO_2$,

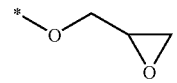

—$NHR_{122}$, —$N(R_{122})_2$, —OH, —$OR_{122}$, —$COR_{122}$;

with the proviso that at least one of $R_{101}$ and $R_{102}$ is not hydrogen;

wherein * denotes the point of attachment;

$R_{122}$ is straight or branched chain $C_1$-$C_{18}$ alkyl, straight or branched chain $C_2$-$C_{18}$ alkenyl, $C_5$-$C_{10}$ cycloalkyl, phenyl, naphthyl, or $C_7$-$C_{15}$ phenylalkyl; and $R_{103}$ is a direct bond, $C_1$-$C_{24}$alkylene, $C_5$-$C_{12}$cycloalkylene, phenylene, $C_1$-$C_6$alkylene-phenylene, phenylene-$C_1$-$C_6$alkylene or $C_1$-$C_6$alkylene-phenylene-$C_1$-$C_6$alkylene.

The alkyl radicals in the various substituents may be linear or branched. Examples of alkyl containing 1 to 24 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

$C_5$-$C_{12}$cycloalkyl is typically, cyclopentyl, methylcyclopentyl, dimethylcyclopentyl, cyclohexyl, methylcyclohexyl.

$C_5$-$C_{12}$cycloalkenyl is for example cyclopentenyl, cyclohexenyl, cycloheptenyl, cyclooctenyl, bicyclo[2.2.1]hept-2-enyl including their isomers.

$C_2$-$C_{18}$alkenyl is for example propenyl, butenyl, pentenyl, hexenyl, heptenyl, octenyl, dodecenyl including their isomers.

$C_2$-$C_{18}$alkyl interrupted by at least one O atom is for example —$CH_2$—$CH_2$—O—$CH_2$—$CH_3$, —$CH_2$—$CH_2$—O—$CH_3$ or —$CH_2$—$CH_2$—O—$CH_2$—$CH_2$—$CH_2$—O—$CH_2$—$CH_3$. It is preferably derived from polyethlene glycol. A general description is —$((CH_2)_a$—$O)_b$—H/$CH_3$, wherein a is a number from 1 to 6 and b is a number from 2 to 10.

Any $C_2$-$C_{24}$alkylene radicals are, for example, ethylene, propylene, 2,2-dimethylpropylene, tetramethylene, hexamethylene, octamethylene, decamethylene or dodecamethylene.

Hydroxyl-, cyano-, alkoxycarbonyl- or carbamide-substituted $C_1$-$C_{24}$alkyl can be, for example, 2-hydroxyethyl, 2-hydroxypropyl, 2-cyanoethyl, methoxycarbonylmethyl, 2-ethoxycarbonylethyl, 2-aminocarbonylpropyl or 2-(dimethylaminocarbonyl)ethyl.

When a diketone or dialdehyde is used dimeric nitroxyl ethers may be obtained which are linked by the group $R_3$ of formula (Ib). Schematically products of the type N—O—$R_3$—O—N can be prepared, particularly when $R_3$ is a longer alkyl spacer group. When $R_3$ is a direct bond N—O-acyl compounds may be obtained.

In particular the ketone or aldehyde is of formula (Ia)

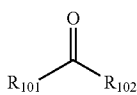

(Ia)

wherein $R_{101}$ and $R_{102}$ are hydrogen, straight or branched chain $C_1$-$C_{24}$alkyl, straight or branched chain $C_2$-$C_{18}$alkenyl, $C_2$-$C_{18}$alkylnyl, $C_5$-$C_{12}$cycloalkyl, $C_5$-$C_{12}$cycloalkenyl, phenyl, naphthyl or $C_7$-$C_{15}$-phenylalkyl which may be unsubstituted or substituted by 1 to 3 OH groups.

Preferably $R_{101}$ and $R_{102}$ are hydrogen, straight or branched chain $C_1$-$C_{12}$alkyl, which alkyl may be unsubstituted or substituted by 1 OH group.

Individual aldehydes and ketones which are particularly useful in the instant process are acetaldehyde, propionaldehyde, butyraldehyde, pentanealdehyde, hexanealdehyde, 2-ethylhexanal, cyclohexylcarboxaldehyde, cyclohexenylcarboxaldehyde, nonaldehyde, pivalaldehyde, 2-phenylpropionaldehyde, phenylacetaldehyde, methoxyacetaldehyde, pyruvic aldehyde, aceton, methylethylketone, diethylketone, 3,3-Dimethyl-2,4-pentanedione, diisopropylketone, methyl isopropylketone, methyl n-propylketone, methyl cyclohexylketone, methyl octylketone in its different isomers, 2-methylacetoacetic acid esters, methoxyacetone, acetylacetaldehyde dimethyl acetal, acetyl acetone, methyl acetoacetate, dimethyl(2-oxopropyl)phosphonate, methanesulfonylacetone, hydroxy-2-methyl-pentanone and methyl pyruvate.

Principally when asymmetric ketones are employed in the reaction the radical with the higher stability is preferentially formed and recombines with the nitroxyl radical. For example, when methyl isopropyl ketone is used the nitroxyl isopropyl ether is formed with high selectivity, typically in a ratio of 1:10.

The ketone or aldehyde can also be prepared and reacted in situ. For example the corresponding alcohol is oxidized with an excess of hydroperoxide in the presence of a suitable catalyst and the resulting aldehyde or ketone is reacted in situ with a hydroperoxide and the same or a second catalyst to yield alkyl radicals which can be scavenged by the nitroxyl radical. In some cases a mixture of the alcohol and the ketone or aldehyde can be of advantage as starting materials.

For instance the hydroperoxide is of formula (II)

(II)

wherein $R_{104}$ is hydrogen, $C_5$-$C_{12}$cycloalkyl, $C_1$-$C_{24}$alkyl, phenyl or phenyl substituted by 1-4 $C_1$-$C_4$alkyl groups.

Preferably the hydroperoxide is tert. butyl hydroperoxide, cumyl hydroperoxide or $H_2O_2$.

Particularly preferred is $H_2O_2$.

The hydroperoxide and in particular $H_2O_2$ is typically dissolved in water and may be used in a concentration from 1% to 90% by weight based on the weight of the total solution. Preferably the concentration is between 20% and 70% by weight.

The hydroperoxide and in particular $H_2O_2$ can also be prepared in situ, for example by electrolysis.

The metal catalyst can be chosen from the group of transition metal catalysts or from the group of metal catalysts with Lewis-Acid character or of the group of water soluble ionic compounds and is preferably selected from the group consisting of scandium, titanium, vanadium, chromium, manganese, iron, cobalt, nickel, copper, zinc, gallium, germanium, yttrium, zirconium, niobium, molybdenum, ruthenium, rhodium, palladium, silver, cadmium, indium, tin, antimony, lanthanum, cerium, hafnium, tantalum, tungsten, rhenium, osmium, iridium, platinum, gold, mercury, thallium, lead, bismuth, aluminum, magnesium, calcium, lithium, barium, boron, sodium, potassium, cesium, strontium or combinations thereof.

The metal catalyst can be bound to an organic or inorganic polymer backbone, providing a homogenous or heterogeneous catalytic system.

The metal catalyst mentioned above may contain anionic ligands commonly known in complex chemistry of transition metals, such as anions derived from inorganic or organic acids, examples being halides, e.g. $F^-$, $Cl^-$, $Br^-$ or $I^-$, fluoro complexes of the type $BF_4^-$, $PF_6^-$, $SbF_6^-$ or $AsF_6^-$, anions of oxygen acids, alcoholates or anions of cyclopentadiene or oxides.

Further examples are: sulfate, phosphate, perchlorate, perbromate, periodate, antimonate, arsenate, nitrate, carbonate, the anion of a $C_1$-$C_{30}$-carboxylic acid, such as formate, acetate, trifluoroacetate, trichloroacetate, propionate, butyrate, benzoate, stearate, phenylacetate, mono-, di- or trichloro- or -fluoroacetate, sulfonates, for example methylsulfonate, ethylsulfonate, propylsulfonate, butylsulfonate, trifluoromethylsulfonate (triflate), unsubstituted or $C_1$-$C_4$alkyl-, $C_1$-$C_4$alkoxy- or halo-, especially fluoro-, chloro- or bromo-substituted phenylsulfonate or benzylsulfonate, carboxylates, for example tosylate, mesylate, brosylate, p-methoxy- or p-ethoxyphenylsulfonate, pentafluorophenylsulfonate or 2,4,6-triisopropylsulfonate, phosphonates, for example methylphosphonate, ethylphosphonate, propylphosphonate, butylphosphonate, phenylphosphonate, p-methylphenylphosphonate or benzylphosphonate, and also $C_1$-$C_{12}$-alcoholates, such as straight chain or branched $C_1$-$C_{12}$-alcoholates, e.g. methanolate or ethanolate.

Anionic and neutral ligands may also be present up to the preferred coordination number of the complex cation of the metal catalyst, especially four, five or six. Additional negative charges are counterbalanced by cations, especially monovalent cations such as $Na^+$, $K^+$, $NH_4^+$ or $(C_1-C_4\ alkyl)_4N^+$. These anionic and neutral ligands may be applied to adjust the reactivity of the corresponding transition metal, e.g. in order to diminish the catalyst activity.

The neutral ligands are commonly known in complex chemistry of transition metals. Suitable inorganic ligands are selected from the group consisting of aquo ($H_2O$), amino, nitrogen, carbon monoxide and nitrosyl. Suitable organic ligands are selected from the group consisting of phosphines, e.g. $(C_6H_5)_3P$, $(i-C_3H_7)_3P$, $(C_5H_9)_3P$ or $(C_6H_{11})_3P$, di-, tri-, tetra- and hydroxyamines, such as ethylenediamine, ethylenediaminetetraacetate (EDTA), N,N-dimethyl-N',N'-bis(2-dimethylaminoethyl)-ethylenediamine ($Me_6TREN$), catechol, N,N'-dimethyl-1,2-benzenediamine, 2-(methylamino) phenol, 3-(methylamino)-2-butanol or N,N'-bis(1,1-dimethylethyl)-1,2-ethanediamine, N,N,N',N'',N''-pentamethylenediethyltriamine (PMDETA), $C_1$-$C_8$-glycols or glycerides, e.g. ethylene or propylene glycol or derivatives thereof, e.g. di-, tri- or tetraglyme, and monodentate or bidentate heterocyclic $e^-$ donor ligands.

The metal catalyst, in particular the transition metal catalyst can further contain heterocyclic $e^-$ donor ligands which are derived, for example, from unsubstituted or substituted heteroarenes from the group consisting of furan, thiophene, pyrrole, pyridine, bis-pyridine, picolylimine, phenanthroline, pyrimidine, bis-pyrimidine, pyrazine, indole, salen, coumarone, thionaphthene, carbazole, dibenzofuran, dibenzothiophene, pyrazole, imidazole, benzimidazole, oxazole, thiazole, bis-thiazole, isoxazole, isothiazole, quinoline, bis-quinoline, isoquinoline, bis-isoquinoline, acridine, chromene, phenazine, phenoxazine, phenothiazine, triazine, thianthrene, purine, bis-imidazole and bis-oxazole.

For example the metal catalyst is a salt or a complex of Ag, Mn, Fe, Cu, Zr, Na, Mg, Ca, Al, Pd, In, Bi or Ce in any oxidation state.

For instance the metal catalyst is a salt or a complex of Fe, Cu, Mn, Na, Mg, Pd, In, Zr or Bi in any oxidation state.

Preferably the metal catalyst is a $Fe^{2+}$ or $Fe^{3+}$, a $Cu^+$ or $Cu^{2+}$, a $Na^+$ or a $Ca^{2+}$ salt.

In the case of Na+, the use of halite (road salt, cattle salt) may be advantageous.

The metal catalyst is typically present in an amount of 0.0005 to 10.0 molar equivalents, dependent on the metal. Cu, for instance is preferably used in amounts of 0.0005 to 0.2 molar equivalents and more preferably from 0.005 to 0.05 molar equivalents, based on the molar equivalents of the sterically hindered nitroxyl radical. Na, for instance, is preferably used in amounts from 0.005 to 3.0 molar equivalents and more preferably from 0.01 to 2.0 molar equivalents, based on the molar equivalents of the sterically hindered nitroxyl radical.

The process is typically carried out at normal atmospheric pressure. In the case of aldehydes or ketones with very low boiling points, it may be advantageous to apply pressure during the reaction.

The reaction time is usually short, depending on the sterically hindered nitroxyl radical used. For example the reaction time varies from 0.5 hours to 20 hours, for instance it is from 1 hour to 7 hours.

The reaction is typically carried out at a temperature between 0° and 100° C. depending on the catalyst used. For instance, if Cu is used, the reaction temperature is in particular between 10° and 60° C. and preferably between 25° and 50° C. If Na is used, the reaction temperature is preferably between 25 and 120° C., more preferably between 60 and 100° C.

The pH value may vary from 1 to 10. Preferably it is neutral to slightly acidic, for instance pH 4 to 6. In the case of ketones the pH is preferably between 2.5 and 4.

A variety of inorganic and organic acids may be used to keep the pH value in the preferred range, examples for inorganic and organic acids have already been mentioned above. Typical examples are HCl, $H_2SO_4$, $H_3PO_4$, $CH_3COOH$, $CH_3SO_3H$ or buffer systems based, for example, on $H_3PO_4$ or $CH_3COOH$.

The reaction can be carried out with or without additional solvent. In some cases it may be of advantage when the reaction is carried out in a two phase system, for instance one phase being water. Two phase systems may also prevail in those cases, where the aldehyde or ketone is not completely soluble in the aqueous phase. The sterically hindered nitroxyl radical may be either in the aqueous phase or in the organic phase and the ketone or aldehyde in the respective other phase. In the case of immiscible phases, it may be advantageous to apply either a phase transfer catalyst, typically an amphiphilic molecule or a suitable inert cosolvent. Typical phase transfer catalysts are salts containing anions, such as halides, hydroxides, hydrogensulfates, phosphates of tetraalkylammonium and alkyl arylphosphonium compounds. Current examples of phase transfer processes can be found, for example, in the Chemical Industry Digest (2005), 18 (7), 49-62, Topics in Catalysis (2004), 29 (3-4), 145-161 or in Interfacial Catalysis (2003), 159-201.

Typical inert solvents are for example, water, alkanes, toluene, xylene, nitrobenzene, acetic acid, esters such as ethyl acetate, alcohols such as ethanol or tert-butanol, halogenated solvents such as methylene chloride or chlorobenzene, ionic liquids, ethers such as tetrahydrofuran or tert.-butylmethylether, NMP or supercritical carbon dioxide. Basically, all hydroperoxide-stable (e.g. hydrogen peroxide stable) solvents may be used in this process. As mentioned before alcohols may be used as co-solvents in the present process, in particular those which form the employed aldehyde or ketone upon oxidation. For instance, ethanol can be used in such processes, where the radical-forming species is acetaldehyde.

The aldehyde or ketone and the hydroperoxide can be used in a wide concentration range. They are typically used in an excess amount, compared to the sterically hindered nitroxyl radical. Typically for the aldehyde or ketone is an excess of 1.05 to 20 mol equivalents, for example 1.25 to 5 mol equivalents, based on the molar amount of the sterically hindered nitroxyl radical. The hydroperoxide is typically used in an excess of 1 to 10 mol equivalents, for example 1.5 to 3 mol equivalents, based on the molar amount of the sterically hindered nitroxyl radical.

The reaction can be carried out in several ways. For instance the sterically hindered nitroxyl radical is dissolved in the aldehyde or ketone. If necessary an inert cosolvent is added. To this solution an aqueous solution of the hydroperoxide is added and after a short time of stirring the metal catalyst is added either dissolved in water or in an appropriate solvent or directly, for example, in the form of a powder. The mixture is stirred and reacted for an appropriate time. In another embodiment of the process it is possible to dissolve the aldehyde or ketone in an appropriate solvent and to add the hydroperoxide subsequently. After a certain time the hindered nitroxide radical is added, either dissolved in an appropriate solvent or neat, followed by the catalyst. It is also possible to dissolve the hindered nitroxyl radical in an appropriate solvent, adding the catalyst and then adding the aldehyde or ketone and the hydroperoxide over the course of time—either simultaneously or one after another. Preferably, the oxidant is added over the course of time to a solution of the hindered nitroxyl radical and the aldehyde or ketone and the metal catalyst in an appropriate solvent or the oxidant and the aldehyde or ketone are added over the course of time to a solution of the hindered nitroxyl radical and the metal catalyst.

It is possible to employ at the beginning the whole amount of aldehyde/ketone or only a part of it. The remaining amount can then be dosed to the reaction mixture over the desired time. The hydroperoxide and the metal catalyst can as well be completely added initially to the reaction mixture or added in portions over a certain time.

For example the sterically hindered nitroxyl radical contains a structural element of formula (Xa) or is of formula (Xb)

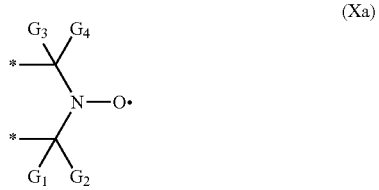
(Xa)

wherein $G_1$, $G_2$, $G_3$ and $G_4$ are independently alkyl of 1 to 4 carbon atoms or $G_1$ and $G_2$ and/or $G_3$ and $G_4$ are together tetramethylene or pentamethylene and * indicates a valence;

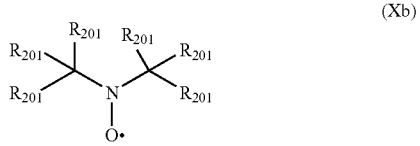
(Xb)

wherein
the $R_{201}$, are each independently of one another hydrogen, halogen, $NO_2$, cyano, $P(O)(OC_2H_5)_2$, —$CONR_{205}R_{206}$, —$(R_{209})COOR_{204}$, —$C(O)$—$R_{207}$, —$OR_{208}$, —$SR_{208}$, —$NHR_{208}$, —$N(R_{208})_2$, carbamoyl, di($C_1$-$C_{18}$alkyl)carbamoyl, —$C(=NR_{205})(NHR_{206})$;
unsubstituted $C_1$-$C_{18}$alkyl, $C_2$-$C_{18}$alkenyl, $C_2$-$C_{18}$alkynyl, $C_7$-$C_9$-phenylalkyl, $C_3$-$C_{12}$cycloalkyl or $C_2$-$C_{12}$heterocycloalkyl; or
$C_1$-$C_{18}$alkyl, $C_2$-$C_{18}$alkenyl, $C_2$-$C_{18}$alkynyl, $C_7$-$C_9$-phenylalkyl, $C_3$-$C_{12}$cycloalkyl or $C_2$-$C_{12}$heterocycloalkyl, which are substituted by $NO_2$, halogen, amino, hydroxy, cyano, carboxy, $C_1$-$C_4$alkoxy, $C_1$-$C_4$alkylthio, $C_1$-$C_4$alkylamino or di($C_1$-$C_4$alkyl)amino; or
phenyl, naphthyl, which are unsubstituted or substituted by $C_1$-$C_4$alkyl, $C_1$-$C_4$alkoxy, $C_1$-$C_4$alkylthio, halogen, cyano, hydroxy, carboxy, $C_1$-$C_4$alkylamino or di($C_1$-$C_4$alkyl)amino;
$R_{204}$ is hydrogen, $C_1$-$C_{18}$alkyl, phenyl, an alkali metal cation or a tetraalkylammonium cation;

$R_{205}$ and $R_{206}$ are hydrogen, $C_1$-$C_{18}$alkyl, $C_2$-$C_{18}$alkyl which is substituted by at least one hydroxy group or, taken together, form a $C_2$-$C_{12}$alkylene bridge or a $C_2$-$C_{12}$-alkylene bridge interrupted by at least one O or/and $NR_{207}$ atom;

$R_{207}$ is hydrogen, $C_1$-$C_{18}$alkyl or phenyl;

$R_{208}$ is hydrogen, $C_1$-$C_{18}$alkyl or $C_2$-$C_{18}$alkyl which is substituted by at least one hydroxy group;

$R_{209}$ is $C_1$-$C_{12}$alkylene or a direct bond;

or all $R_{201}$ form together the residue of a polycyclic cycloaliphatic ring system or a polycyclic heterocycloaliphatic ring system with at least one di- or trivalent nitrogen atom.

In general sterically hindered nitroxyl radicals containing a structural element of formula (Xa) are preferred.

For instance the sterically hindered nitroxyl radical is of formula (Xb) or (Xc)

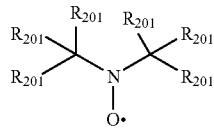
(Xb)

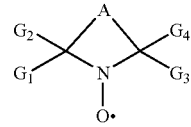
(Xc)

wherein
the $R_{201}$, are each independently of one another hydrogen, halogen, $NO_2$, cyano, $P(O)(OC_2H_5)_2$, —$CONR_{205}R_{206}$, —$(R_{209})COOR_{204}$, —$C(O)$—$R_{207}$, —$OR_{208}$, —$SR_{208}$, —$NHR_{208}$, —$N(R_{208})_2$, carbamoyl, di($C_1$-$C_{18}$alkyl)carbamoyl, —$C(=NR_{205})(NHR_{206})$;
unsubstituted $C_1$-$C_{18}$alkyl, $C_2$-$C_{18}$alkenyl, $C_2$-$C_{18}$alkynyl, $C_7$-$C_9$-phenylalkyl, $C_3$-$C_{12}$cycloalkyl or $C_2$-$C_{12}$heterocycloalkyl; or
$C_1$-$C_{18}$alkyl, $C_2$-$C_{18}$alkenyl, $C_2$-$C_{18}$ alkynyl, $C_7$-$C_9$-phenylalkyl, $C_3$-$C_{12}$cycloalkyl or $C_2$-$C_{12}$heterocycloalkyl, which are substituted by $NO_2$, halogen, amino, hydroxy, cyano, carboxy, $C_1$-$C_4$alkoxy, $C_1$-$C_4$alkylthio, $C_1$-$C_4$alkylamino or di($C_1$-$C_4$alkyl)amino; or phenyl, naphthyl, which are unsubstituted or substituted by $C_1$-$C_4$alkyl, $C_1$-$C_4$alkoxy, $C_1$-$C_4$alkylthio, halogen, cyano, hydroxy, carboxy, $C_1$-$C_4$alkylamino or di($C_1$-$C_4$alkyl)amino;

$R_{204}$ is hydrogen, $C_1$-$C_{18}$alkyl, phenyl, an alkali metal cation or a tetraalkylammonium cation;

$R_{205}$ and $R_{206}$ are hydrogen, $C_1$-$C_{18}$alkyl, $C_2$-$C_{18}$alkyl which is substituted by at least one hydroxy group or, taken together, form a $C_2$-$C_{12}$alkylene bridge or a $C_2$-$C_{12}$-alkylene bridge interrupted by at least one O or/and $NR_8$ atom;

$R_{207}$ is hydrogen, $C_1$-$C_{18}$alkyl or phenyl;

$R_{208}$ is hydrogen, $C_1$-$C_{18}$alkyl or $C_2$-$C_{18}$alkyl which is substituted by at least one hydroxy group;

$R_{209}$ is $C_1$-$C_{12}$alkylene or a direct bond;

or all $R_{201}$ form together the residue of a polycyclic cycloaliphatic ring system or a polycyclic heterocycloaliphatic ring system with at least one di- or trivalent nitrogen atom;

G₁, G₂, G₃ and G₄ are independently alkyl of 1 to 4 carbon atoms or G₁ and G₂ and/or G₃ and G₄ are together tetramethylene or pentamethylene; and A is a divalent group required to form a cyclic or heterocyclic 5-, 6- or 7-membered ring, which is unsubstituted or substituted by —OH, =O or by one or two organic residues containing in total 1-500 carbon atoms and optionally 1-200 heteroatoms.

Sterically hindered nitroxyl radicals conforming to formula (Xc) are preferred.

In a preferred process the sterically hindered nitroxyl radical is of formula (A) to (O)

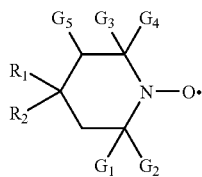
(A)

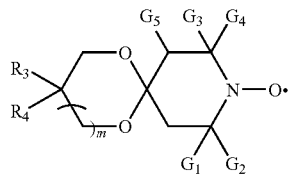
(B)

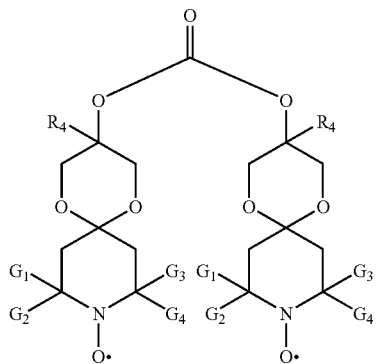
(B′)

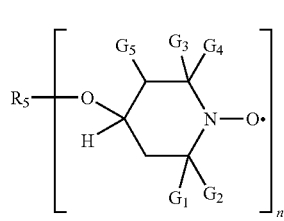
(C)

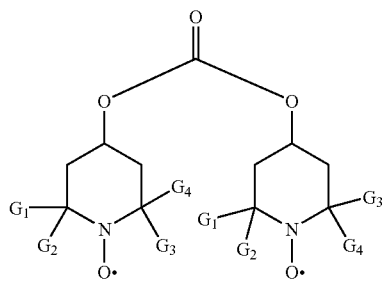
(C′)

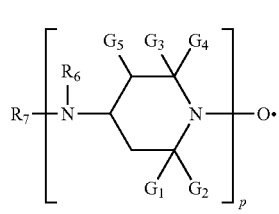
(D)

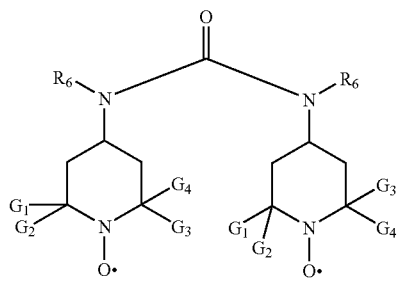
(D′)

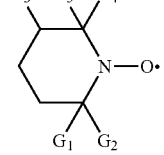
(E)

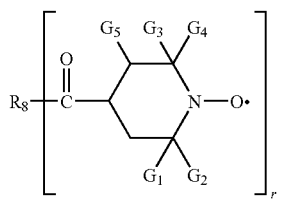
(F)

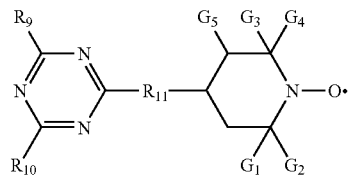
(G)

-continued

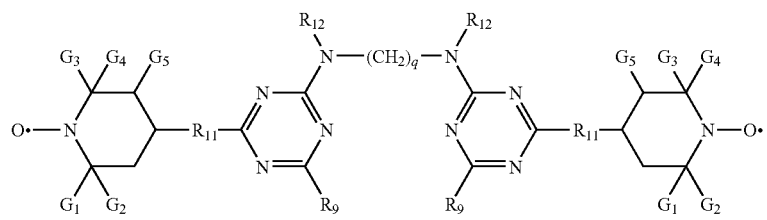
(H)

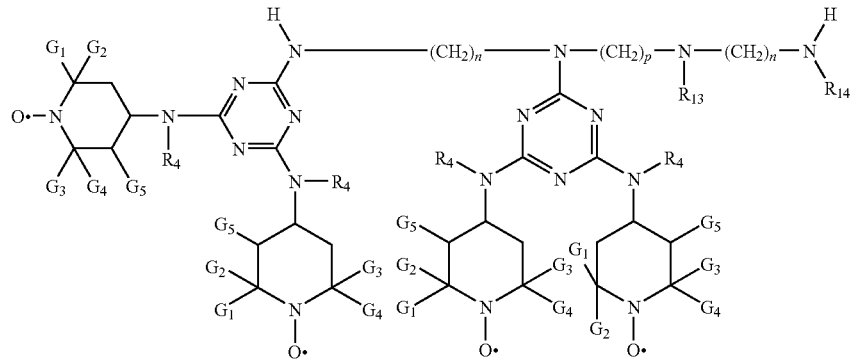
(I)

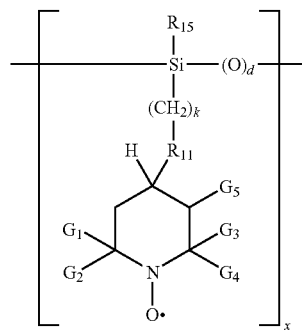
(K)

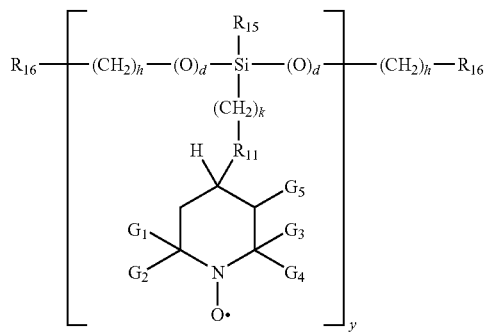
(L)

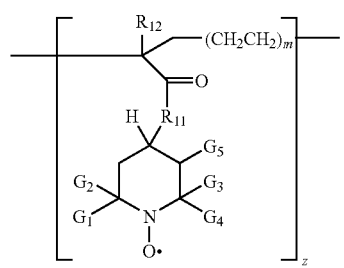
(M)

(N)

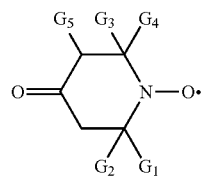
(O)

wherein
$G_1, G_2, G_3, G_4$ are independently $C_1$-$C_4$alkyl and $G_5$ is hydrogen or methyl;
$R_1$ is H and $R_2$ is OH;
m is 0 or 1;
$R_3$ is hydrogen, hydroxyl or hydroxymethyl, $C_1$-$C_{22}$alkanoyl, $C_1$-$C_{22}$alkoxycarbonyl, $C_1$-$C_{22}$alkanoyloxy;
$R_4$ is hydrogen, alkyl of 1 to 12 carbon atoms or alkenyl of 2 to 12 carbon atoms;

n is 1 to 4;
when n is 1,
$R_5$ is hydrogen, alkyl of 1 to 18 carbon atoms, alkoxycarbonylalkylenecarbonyl of 4 to 18 carbon atoms, alkenyl of 2 to 18 carbon atoms, glycidyl, 2,3-dihydroxypropyl, 2-hydroxy or 2-(hydroxymethyl) substituted alkyl of 3 to 12 carbon atoms which alkyl is interrupted by oxygen, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, or acyl radical of an aromatic acid containing 7 to 15 carbon atoms;

when n is 2, $R_5$ is alkylene of 2 to 18 carbon atoms, a divalent acyl radical of an aliphatic or unsaturated aliphatic dicarboxylic or dicarbamic acid containing 2 to 18 carbon atoms, a divalent acyl radical of a cycloaliphatic dicarboxylic or dicarbamic acid containing 7 to 12 carbon atoms, or a divalent acyl radical of an aromatic dicarboxylic acid containing 8 to 15 carbon atoms;

when n is 3, $R_5$ is a trivalent acyl radical of an aliphatic or unsaturated aliphatic tricarboxylic acid containing 6 to 18 carbon atoms, or a trivalent acyl radical of an aromatic tricarboxylic acid containing 9 to 15 carbon atoms;

when n is 4, $R_5$ is a tetravalent acyl radical of an aliphatic or unsaturated aliphatic tetracarboxylic acid, especially 1,2,3,4-butanetetracarboxylic acid, 1,2,3,4-but-2-enetetracarboxylic acid, 1,2,3,5-pentanetetracarboxylic acid and 1,2,4,5-pentanetetracarboxylic acid, or $R_5$ is a tetravalent acyl radical of an aromatic tetracarboxylic acid containing 10 to 18 carbon atoms;

p is 1 to 3;

$R_6$ is hydrogen, alkyl of 1 to 18 carbon atoms or acyl of 2 to 6 carbon atoms or phenyl;

when p is 1, $R_7$ is hydrogen, phenyl, alkyl of 1 to 18 carbon atoms, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, an acyl radical of an aromatic carboxylic acid containing 7 to 15 carbon atoms, or $R_6$ and $R_7$ together are $-(CH_2)_5CO-$, phthaloyl or a divalent acyl radical of maleic acid;

when p is 2, $R_7$ is alkylene of 2 to 12 carbon atoms, a divalent acyl radical of an aliphatic or unsaturated aliphatic dicarboxylic or dicarbamic acid containing 2 to 18 carbon atoms, a divalent acyl radical of a cycloaliphatic dicarboxylic or dicarbamic acid containing 7 to 12 carbon atoms, or a divalent acyl radical of an aromatic dicarboxylic acid containing 8 to 15 carbon atoms;

when p is 3, $R_7$ is a trivalent acyl radical of an aliphatic or unsaturated aliphatic tricarboxylic acid containing 6 to 18 carbon atoms, or a trivalent acyl radical of an aromatic tricarboxylic acid containing 9 to 15 carbon atoms;

r is 1 to 4;

when r is 1, $R_8$ is alkoxy of 1 to 18 carbon atoms, alkenyloxy of 2 to 18 carbon atoms, $-NHalkyl$ of 1 to 18 carbon atoms or $-N(alkyl)_2$ of 2 to 36 carbon atoms;

when r is 2, $R_8$ is alkylenedioxy of 2 to 18 carbon atoms, alkenylenedioxy of 2 to 18 carbon atoms, $-NH$-alkylene-$NH-$ of 2 to 18 carbon atoms or $-N(alkyl)$-alkylene-$N(alkyl)$- of 2 to 18 carbon atoms, or $R_8$ is 4-methyl-1,3-phenylenediamino;

when r is 3, $R_8$ is a trivalent alkoxy radical of a saturated or unsaturated aliphatic triol containing 3 to 18 carbon atoms;

when r is 4, $R_8$ is a tetravalent alkoxy radical of a saturated or unsaturated aliphatic tetraol containing 4 to 18 carbon atoms;

$R_9$ and $R_{10}$ are independently chlorine, alkoxy of 1 to 18 carbon atoms, $-O-T_1$, amino substituted by 2-hydroxyethyl, $-NH(alkyl)$ of 1 to 18 carbon atoms, $-N(alkyl)T_1$ with alkyl of 1 to 18 carbon atoms, or $-N(alkyl)_2$ of 2 to 36 carbon atoms;

$R_{11}$ is oxygen, or $R_{11}$ is nitrogen substituted by either hydrogen, alkyl of 1 to 12 carbon atoms or $T_1$;

$T_1$ is 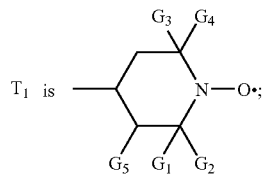

$R_{12}$ is hydrogen or methyl;

q is 2 to 8;

$R_{13}$ and $R_{14}$ are independently hydrogen or the group $T_2$;

$T_2$ is 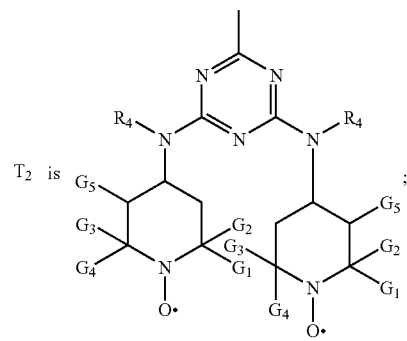 ;

$R_{15}$ is hydrogen, phenyl, straight or branched alkyl of 1 to 12 carbon atoms, alkoxy of 1 to 12 carbon atoms, straight or branched alkyl of 1 to 4 carbon atoms substituted by phenyl, cycloalkyl of 5 to 8 carbon atoms, cycloalkenyl of 5 to 8 carbon atoms, alkenyl of 2 to 12 carbon atoms, glycidyl, allyloxy, straight or branched hydroxyalkyl of 1 to 4 carbon atoms, or silyl or silyloxy substituted three times independently by hydrogen, by phenyl, by alkyl of 1 to 4 carbon atoms or by alkoxy of 1 to 4 carbon atoms;

$R_{16}$ is hydrogen or silyl substituted three times independently by hydrogen, by phenyl, by alkyl of 1 to 4 carbon atoms or by alkoxy of 1 to 4 carbon atoms;

d is 0 or 1;

h is 0 to 4;

k is 0 to 5;

x is 3 to 6;

y is 1 to 10;

z is an integer such that the compound has a molecular weight of 1000 to 4000 amu, e.g. z may be from the range 3-10;

$R_{17}$ is morpholino, piperidino, 1-piperizinyl, alkylamino of 1 to 8 carbon atoms, especially branched alkylamino of 3 to 8 carbon atoms such as tert-octylamino, $-N(alkyl)T_1$ with alkyl of 1 to 8 carbon atoms, or $-N(alkyl)_2$ of 2 to 16 carbon atoms;

$R_{18}$ is hydrogen, acyl of 2 to 4 carbon atoms, carbamoyl substituted by alkyl of 1 to 4 carbon atoms, s-triazinyl substituted once by chlorine and once by $R_{17}$, or s-triazinyl substituted twice by $R_{17}$ with the condition that the two $R_{17}$ substituents may be different;

$R_{19}$ is chlorine, amino substituted by alkyl of 1 to 8 carbon atoms or by $T_1$, $-N(alkyl)T_1$ with alkyl of 1 to 8 carbon atoms, $-N(alkyl)_2$ of 2 to 16 carbon atoms, or the group $T_3$;

T₃ is 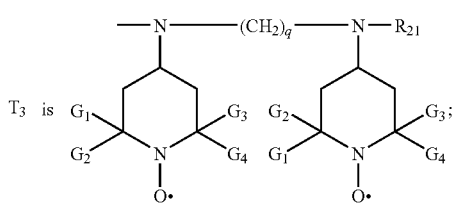

and

R₂₁ is hydrogen, acyl of 2 to 4 carbon atoms, carbamoyl substituted by alkyl of 1 to 4 carbon atoms, s-triazinyl substituted twice by —N(alkyl)₂ of 2 to 16 carbon atoms or s-triazinyl substituted twice by —N(alkyl)T₁ with alkyl of 1 to 8 carbon atoms.

In the definitions the term alkyl comprises within the given limits of carbon atoms, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, 2-methylheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl or dodecyl.

Examples of alkenyl are within the given limits of carbon atoms vinyl, allyl, and the branched and unbranched isomers of butenyl, pentenyl, hexenyl, heptenyl, octenyl, nonenyl, decenyl, undecenyl and dodecenyl. The term alkenyl also comprises residues with more than one double bond that may be conjugated or non-conjugated, for example may comprise one double bond.

Examples of alkinyl are within the given limits of carbon atoms ethinyl and propinyl and unbranched isomers of butinyl, pentinyl, hexinyl, heptinyl, octinyl, noninyl, decinyl, undecinyl and dodecinyl. The term alkinyl also comprises residues with more than one triple bond that may be conjugated or non-conjugated and residues with at least one triple bond and at least one double bond, for example comprises residues with one triple bond.

Examples of alkylene are within the given limits of carbon atoms branched and unbranched isomers of vinylene, allylene, butylene, pentylene, hexylene, heptylene, octylene, nonylene, decylene, undecylene and dodecylene.

Some examples of cycloalkyl are cyclopentyl, cyclohexyl, methylcyclopentyl, dimethylcyclopentyl and methylcyclohexyl.

Some examples of cycloalkenyl are cyclopentenyl, cyclohexenyl, methylcyclopentenyl, dimethylcyclopentenyl and methylcyclohexenyl. Cycloalkenyl may comprise more than one double bond that may be conjugated or non-conjugated, for example may comprise one double bond.

Aryl is for example phenyl or naphthyl.

Aralkyl is for instance benzyl or α,α-dimethylbenzyl.

The term alkoxy may comprise within the limits of the given number of carbon atoms, for example methoxy and ethoxy and the branched and unbranched isomers of propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy and octadecyloxy.

The term halogen may comprise chlorine, bromine and iodine; for example halogen is chlorine.

The term halide may comprise fluoride, chloride, bromide or iodide.

For instance, alkali metal comprises Li, Na, K, Rb or Cs.

For example, alkaline-earth metal comprises Be, Mg, Ca, Sr or Ba.

Acyl radicals of monocarboxylic acids are, within the definitions, a residue of the formula —CO—R'', wherein R'' may stand inter alia for an alkyl, alkenyl, cycloalkyl or aryl radical as defined. Preferred acyl radicals include acetyl, benzoyl, acryloyl, methacryloyl, propionyl, butyryl, valeroyl, hexanoyl, heptanoyl, octanoyl, nonanoyl, decanoyl, undecanoyl, dodecanoyl, pentadecanoyl, stearoyl. Polyacyl radicals of polyvalent acids are of the formula (—CO)ₙ—R'', wherein n is the valency, e.g. 2, 3 or 4.

Some examples of an aliphatic carboxylic acid are acetic, propionic, butyric, stearic acid. An example of a cycloaliphatic carboxylic acid is cyclohexanoic acid. An example of an aromatic carboxylic acid is benzoic acid. An example of an aliphatic dicarboxylic acid is malonyl, maleoyl or succinyl, or sebacic acid. An example of a residue of an aromatic dicarboxylic acid is phthaloyl.

Preferably G₁ and G₃ are ethyl and G₂, G₄ and G₅ are methyl or G₁ and G₂ are methyl, G₃ and G₄ are ethyl and G₅ is hydrogen or G₁, G₂, G₃ and G₄ are methyl and G₅ is hydrogen.

More preferred G₁, G₂, G₃ and G₄ are methyl and G₅ is hydrogen.

Preferably the sterically hindered nitroxyl radical is of formula (A), (B), (B'), (C), (C'), (G), (N) or (O), more preferably of formula (C), (G) or (N).

In a preferred embodiment the instant process leads to a sterically hindered nitroxyl ether containing a structural element of formula (XI)

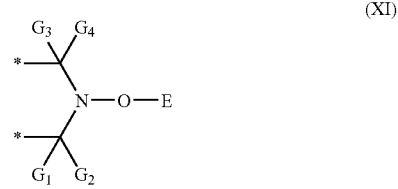

wherein G₁, G₂, G₃ and G₄ are as defined above and E has the meaning of R₁₀₁ or R₁₀₂ as defined above.

Individual compounds which may be prepared by the instant process are for example:

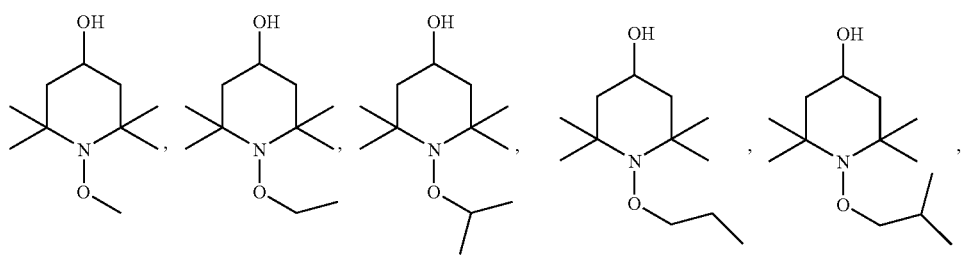

-continued
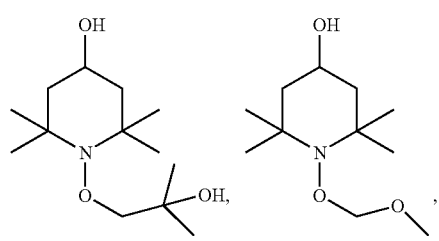 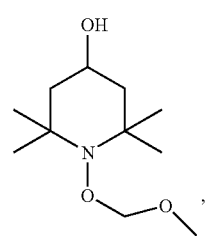 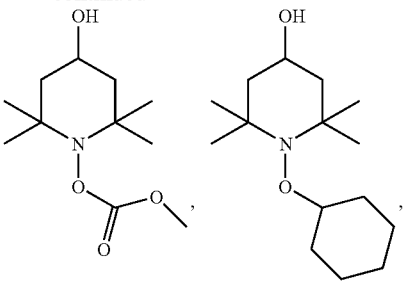 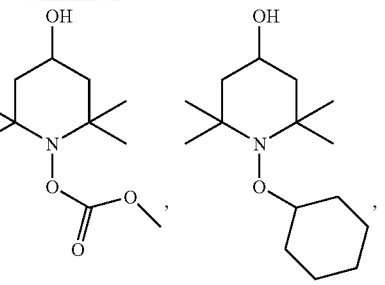
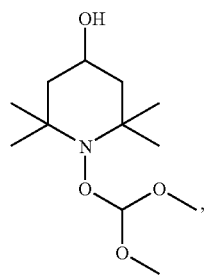 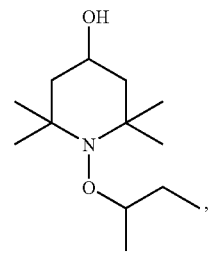 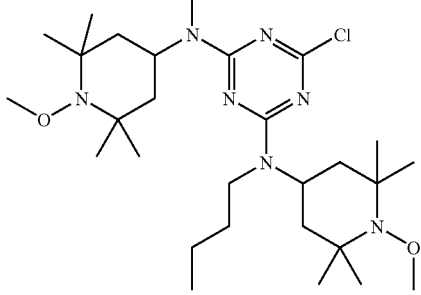
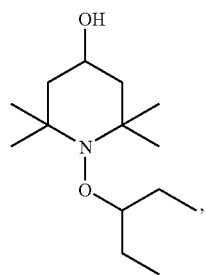 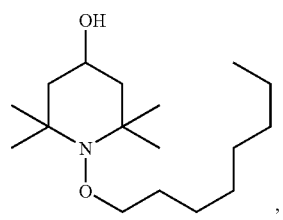 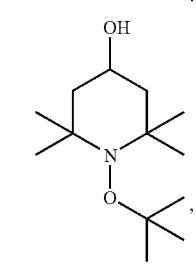
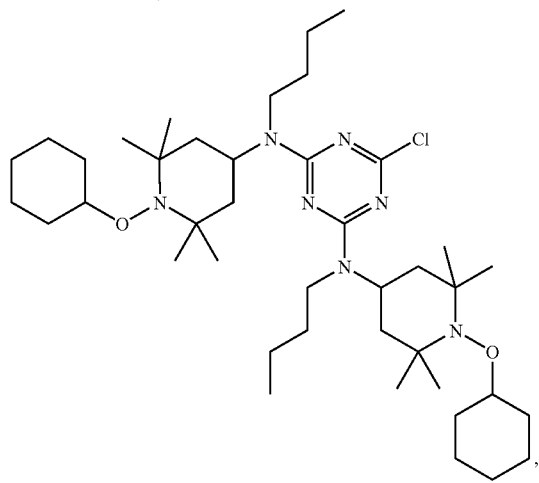 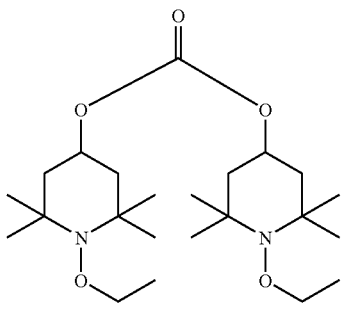
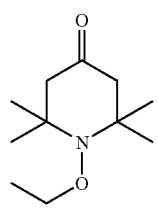 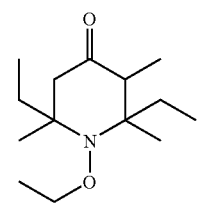 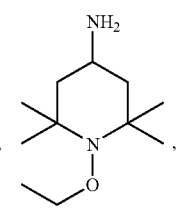 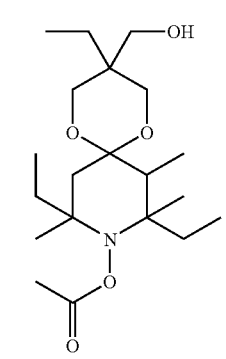 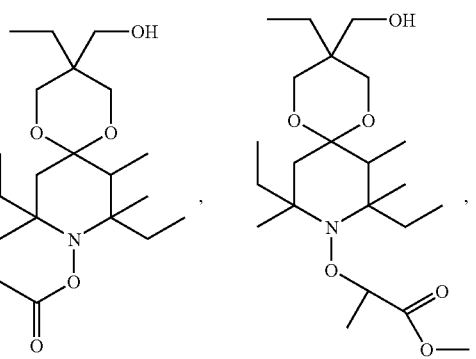

-continued
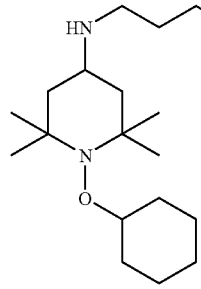 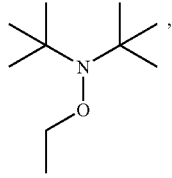 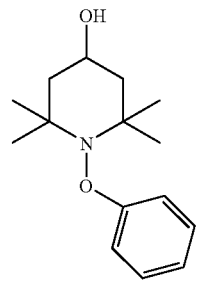 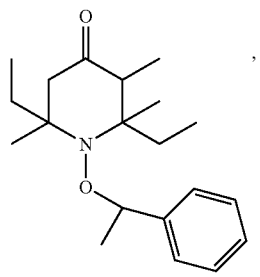
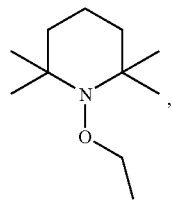 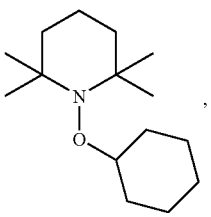 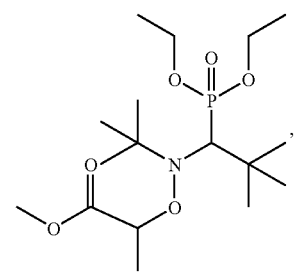 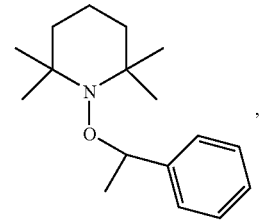
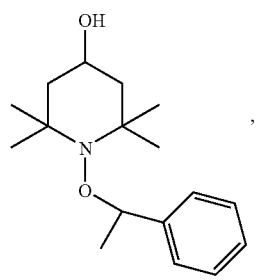 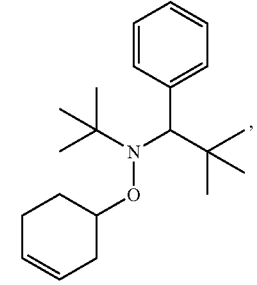 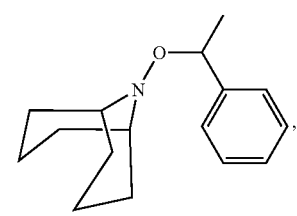 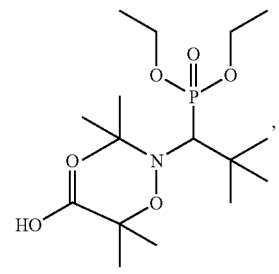
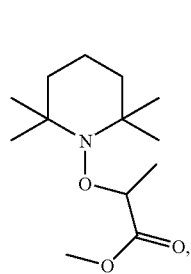 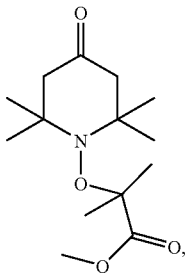 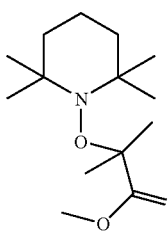 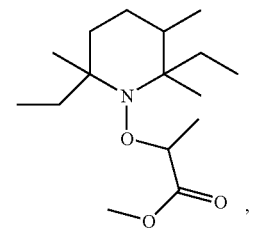 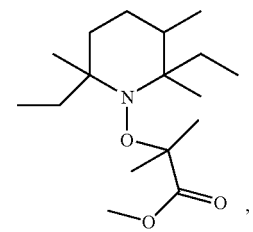
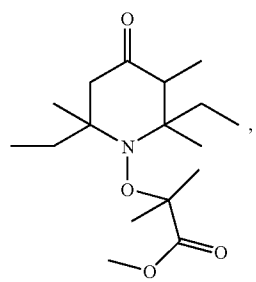 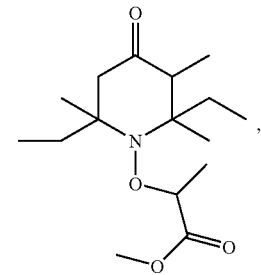 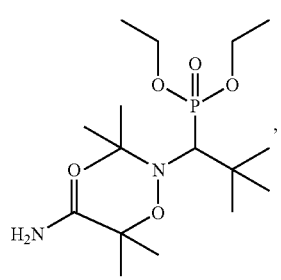 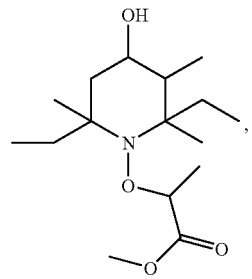

-continued
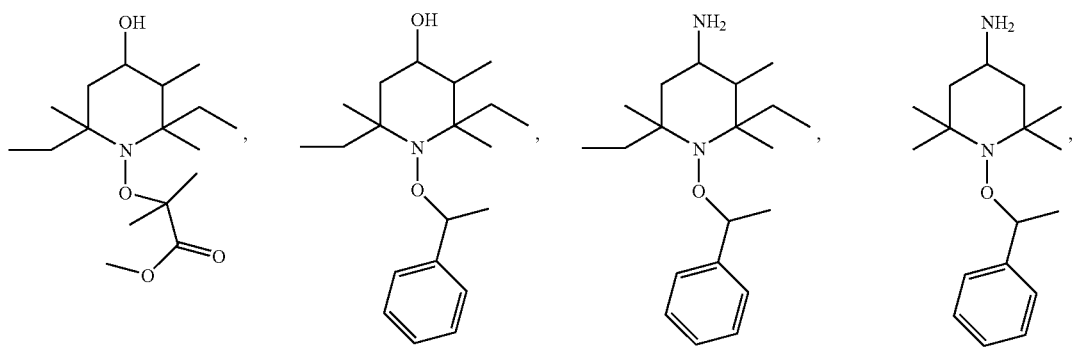
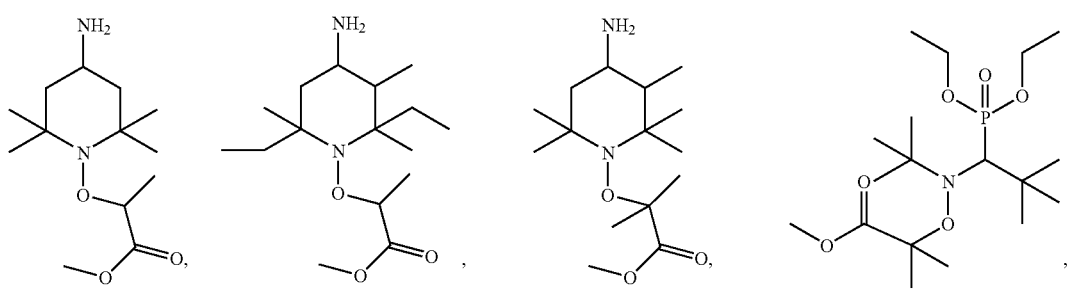
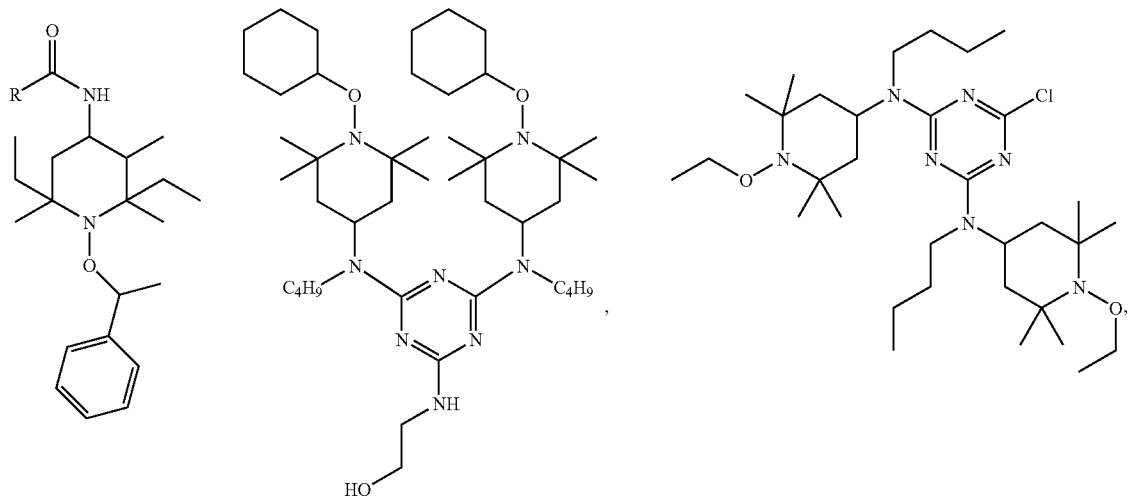
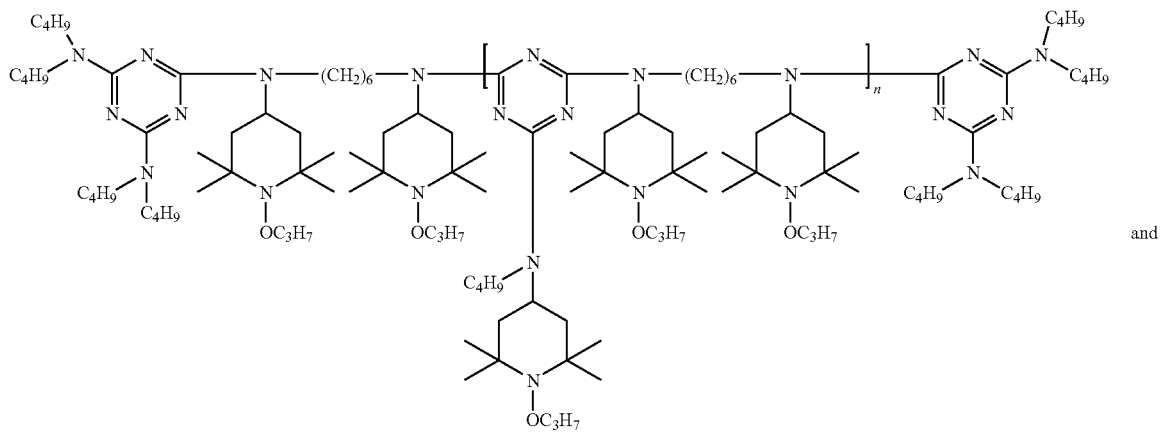
and

-continued
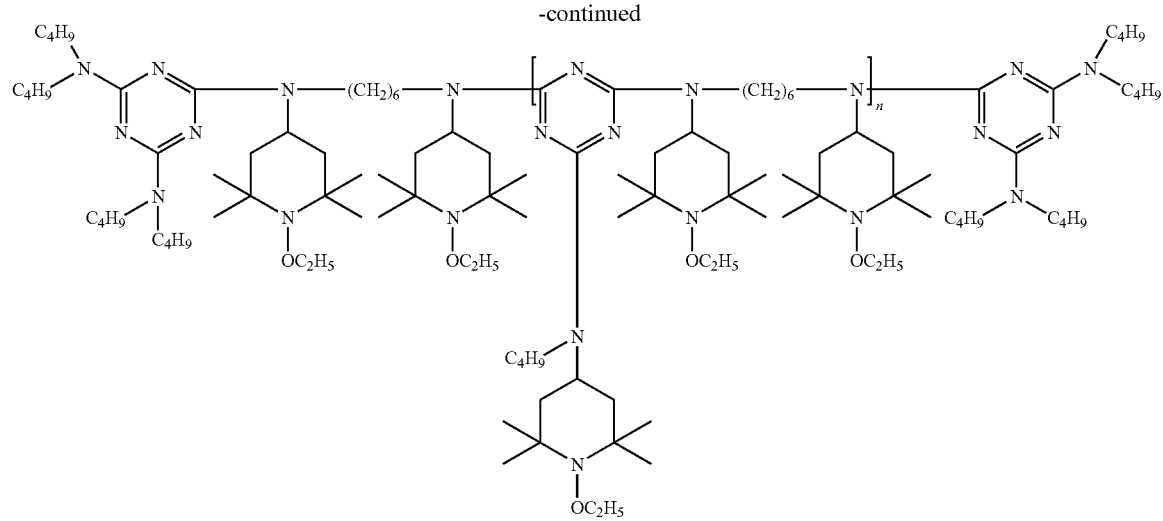
Wherein n is a number from 1 to 10;
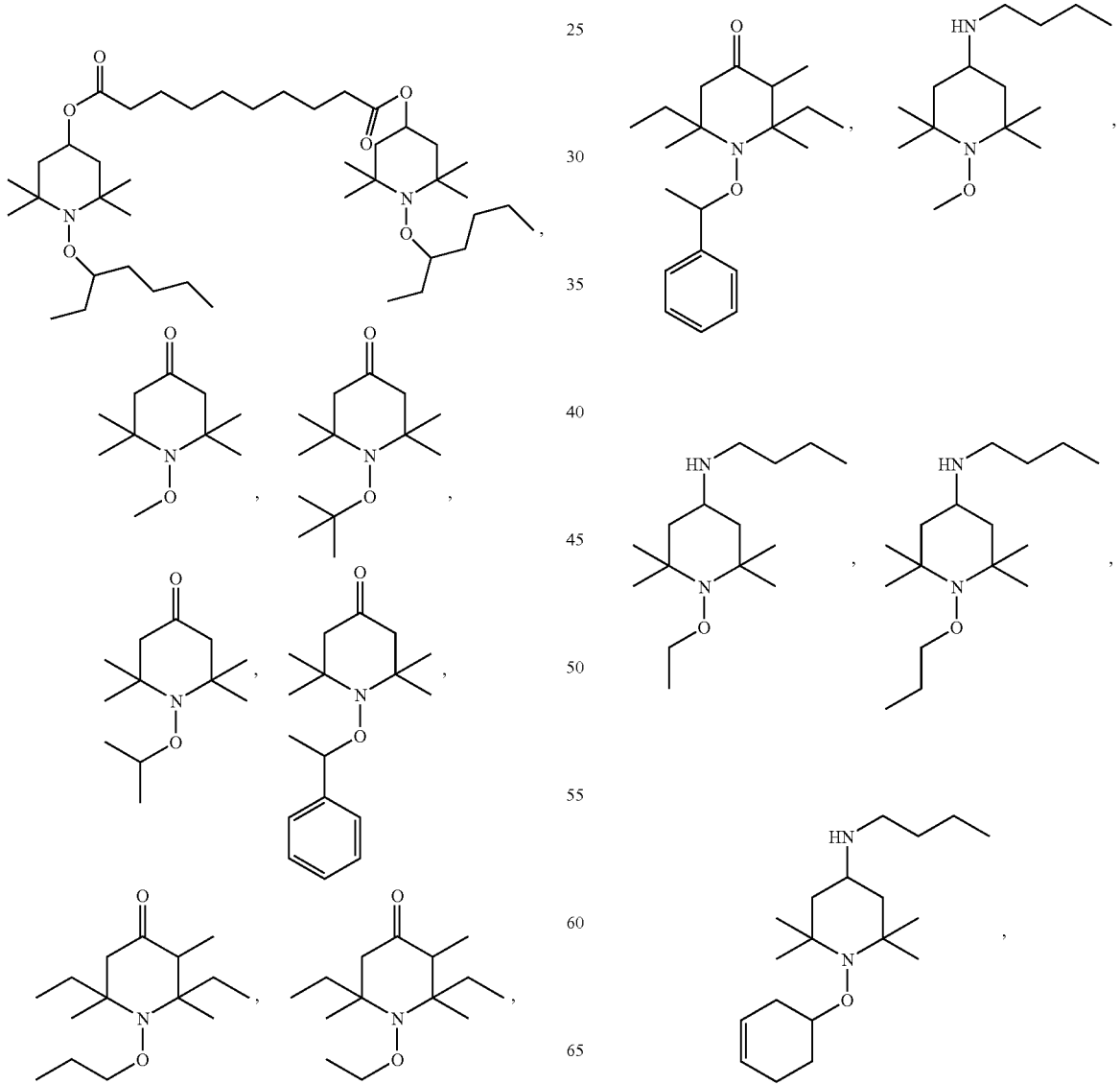

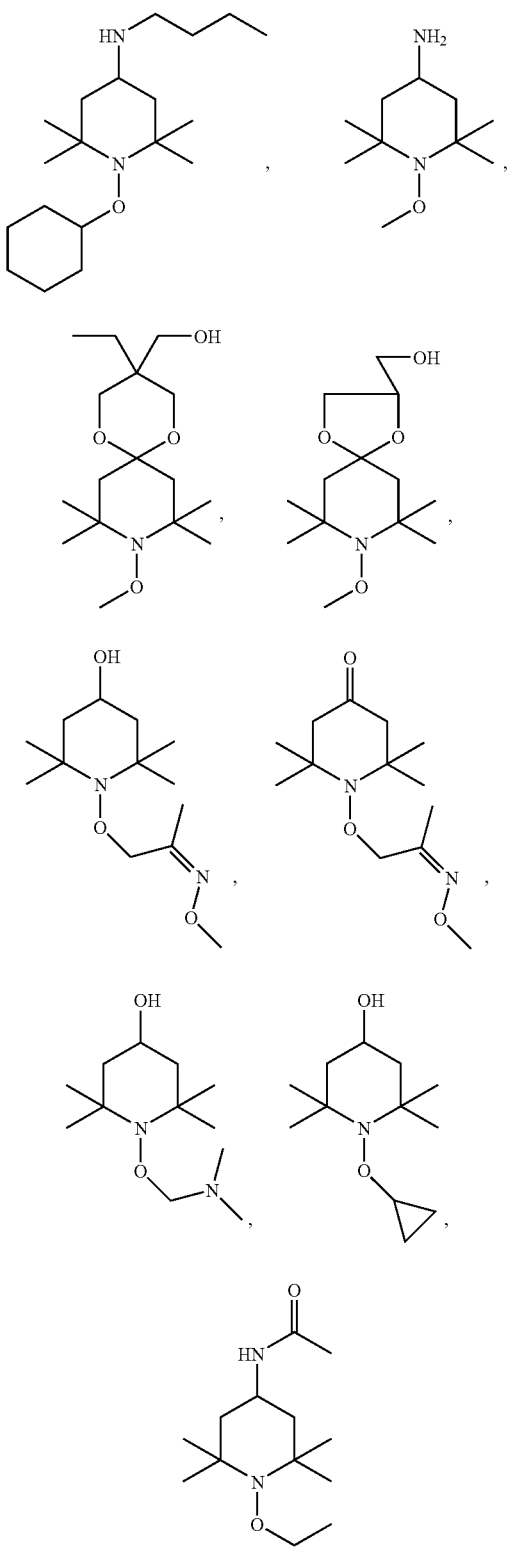

The sterically hindered nitroxyl radicals are largely known in the art; they may be prepared by oxidation of the corresponding N—H sterically hindered amine with a suitable oxygen donor, e.g. by the reaction of the corresponding N—H sterically hindered amine with hydrogen peroxide and sodium tungstate as described by E. G. Rozantsev et al., in Synthesis, 1971, 192; or with tert-butyl hydroperoxide and molybdenum (VI) as taught in U.S. Pat. No. 4,691,015, or obtained in analogous manner.

The precursor compounds of the sterically hindered nitroxyl radicals (sterically hindered NH compounds) are essentially known and partially commercially available. All of them can be prepared by known processes. Their preparation is disclosed, for example, in:

U.S. Pat. Nos. 5,679,733, 3,640,928, 4,198,334, 5,204,473, 4,619,958, 4,110,306, 4,110,334, 4,689,416, 4,408,051, SU-A-768,175 (Derwent 88-138,751/20), U.S. Pat. Nos. 5,049,604, 4,769,457, 4,356,307, 4,619,956, 5,182,390, GB-A-2,269,819, U.S. Pat. Nos. 4,292,240, 5,026,849, 5,071,981, 4,547,538, 4,976,889, 4,086,204, 6,046,304, 4,331,586, 4,108,829, 5,051,458, WO-A-94/12,544 (Derwent 94-177,274/22), DD-A-262,439 (Derwent 89-122, 983/17), U.S. Pat. Nos. 4,857,595, 4,529,760, 4,477,615, CAS 136, 504-96-6, U.S. Pat. Nos. 4,233,412, 4,340,534, WO-A-98/51,690 and EP-A-1,803, in particular U.S. Pat. Nos. 4,442,250 or 6,046,304.

The oxidation may be carried out in analogy to the oxidation of 4-hydroxy-2,2,6,6-tetramethylpiperidine described in U.S. Pat. No. 5,654,434 with hydrogen peroxide. Another also suitable oxidation process is described in WO 00/40550 using peracetic acid. An exhaustive description of the nitroxide (nitroxyl radical) chemistry can be found, for example, in L. B. Volodarsky, V. A. Reznikov, V. I. Ovcharenko.: "Synthetic Chemistry of Stable Nitroxides", CRC Press, 1994.

A further aspect of this process comprises the in situ generation of the nitroxyl compounds starting from the corresponding piperidines. For example, this can be achieved by the intermediate formation of peracids, such as peracetic acid or meta-chloroperbenzoic acid, by using an excess of hydrogen peroxide in the presence of a suitable acid and the ketone/aldehyde. Alternatively, suitable peracids may be employed in the first place to generate the nitroxyl compound, followed by the direct addition of the ketone/aldehyde. The addition of a further metal catalyst which is able to promote the oxidation of the piperidine to the corresponding nitroxyl in the presence of a suitable oxidant, such as hydrogen peroxide, and the ketone/aldehyde, is another possibilty to perform the actual process. Alternatively, a 2-step/one-pot reaction can be performed, for instance by performing the oxidation of the piperidine to the corresponding nitroxyl radical with hydrogen peroxide and a suitable catalyst, such as sodium tungstate or sodium carbonate, followed by the addition of the aldehyde, a suitable catalyst and, if required, additional hydrogen peroxide.

The sterically hindered nitroxyl ethers are useful as light and heat stabilizers, flame retardants and polymerization initiators/regulators.

Further aspects of the invention are the following compounds:

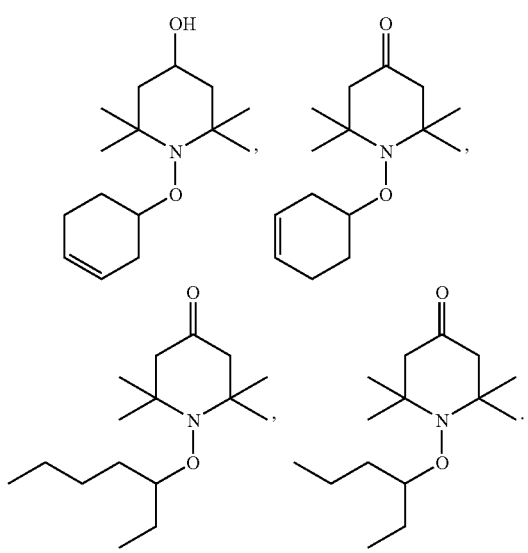

1-cyclohexenyloxy-2,2,6,6-tetramethyl-piperidin-4-ol,
1-cyclohexenyloxy-2,2,6,6-tetramethyl-piperidin-4-one,
1-heptyl-2-oxy-2,2,6,6-tetramethyl-piperidin-4-one and
1-pentyl-2-oxy-2,2,6,6-tetramethyl-piperidin-4-one.

The following examples illustrate the invention.

PREPARATION EXAMPLES

Example 1

Preparation of
1-Ethoxy-2,2,6,6-tetramethyl-piperidin-4-ol,
compound 101

25.1 g (145.1 mmol) 1-oxy-2,2,6,6-tetramethyl-piperidin-4-ol (Prostab 5198, commercial product of Ciba Specialty Chemicals Inc.) are dissolved in 105 ml methyl ethyl ketone and 50 ml (~3 eq.) of a 30% aqueous hydrogen peroxide solution are added over a period of 10 min. Upon cooling to 5° C., 0.71 g (5 mol %) CuCl are added and the temperature of the reaction mixture is kept between 5 and 50° C. After 15-30 minutes the pH of the reaction mixture is adjusted to ~3.5 and the brownish solution is stirred over night at room temperature. A green homogeneous solution is obtained. 250 ml of ethyl acetate are added and the aqueous phase is separated. The organic phase is successively washed with 10% ascorbic acid solution, water, dil. sodium carbonate sol., dil. sodium chloride sol., and saturated sodium chloride sol. A peroxide test indicates only minor amounts of residual hydrogen peroxide. The organic phase is dried over sodium sulfate and finally evaporated to complete dryness under vacuum.

Yield: 22.9 g (114 mmol, 78%), greenish solid. The product contains a mixture of ethyl and methyl substituted product in a ratio of ~9:1.

$^{1}$H-NMR (CDCl$_3$), δ (ppm): 1.12 (t, 3H), 1.15 (s, 3H), 1.19 (s, 3H), 1.42 (m, 4H), 1.80 (dd, 2H), 3.78 (dt, 2H), 3.95 (dddd, 1H).

$^{13}$C-NMR (CDCl$_3$), δ (ppm): 14.0, 21.4, 33.5, 48.7, 60.2, 63.8, 72.7.

Example 2

Preparation of Compound 102

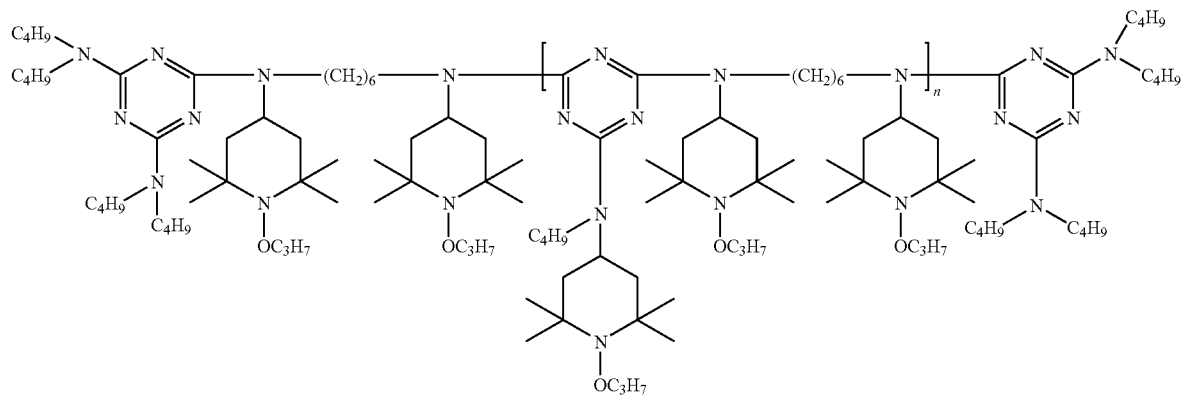

wherein n is a number from 1 to 10,

Compound 102 a) Preparation of the Nitroxyl Radical Precursor 5.3 g of the corresponding NH compound of compound 100 (Chimasorb 2020, a commercial product of Ciba Specialty Chemicals Inc.) are dissolved in 25 ml ethyl acetate. To this solution 10 ml of water and 5.5 g of solid sodium hydrogen carbonate are added. Under thorough stirring, 4.5 ml of a 40% peracetic acid solution in acetic acid are added over 20 min. while keeping the temperature at around 25° C. The reaction mixture turns red after a couple of minutes and is stirred for 3 h. Thereupon, the two phases are separated and the aqueous phase is discarded. The organic phase is diluted with 50 ml ethyl acetate and successively washed with water, diluted sodium carbonate solution and brine. The organic phase is dried over sodium sulfate and evaporated to complete dryness under vacuum.

Yield: 2.9 g; red oil of the corresponding nitroxyl radical.

b) Preparation of the Nitroxyl Propylether, Compound 102

0.8 g of the obtained nitroxyl prepared in step a) are dissolved in 10 ml 2-pentanone and 4 ml 50% aqueous hydrogen peroxide are added at room temperature. The mixture is stirred for 15 min., 30 mg CuCl are added, and the reaction mixture is stirred over night (22 h) at room temp. The two phases are separated and the copper containing aqueous phase is discarded. The organic phase is diluted with 50 ml toluene and successively washed with 10% ascorbic acid solution, 0.5 N sodium hydroxide solution and saturated sodium chloride solution The organic phase is dried over sodium sulfate and evaporated to complete dryness under vacuum (60° C., 0.1 mbar).
Yield: ~500 mg (approx. 60%); pale yellow foam.

Example 3

Preparation of 2-Chloro-4,6-bis[N-[(1-(cyclohexyloxy)-2,2,6,6-tetramethyl-piperidin-4-yl)butylamino]-s-triazine, compound 103 a) Preparation of the 2-Chloro-4,6-bis[N-(1-oxyl-2,2,6,6-tetramethylpiperidin-4-yl)butylamino]-s-triazine precursor
5.4 g (10.1 mmol) N,N'-dibutyl-6-chloro-N,N'-bis(2,2,6,6-tetramethyl-4-piperidinyl)-1,3,5-tri-azine-2,4-diamine are dissolved in 25 ml ethyl acetate. Subsequently, 10 ml of water, 3.5 g sodium hydrogencarbonate and 3.8 g (10.1 mmol) of a 40% peracetic acid solution in acetic acid are added at 0° C. After 4 h at 0° C., another 1.9 g peracetic acid solution are added and the reaction mixture is stirred at 0° C. over night. The mixture is diluted with toluene/hexane and successively washed with water, diluted sodium carbonate solution and brine. The organic phase is dried over sodium sulfate and evaporated to complete dryness to yield 4.0 g (70%) of a red solid.
b) 1.0 g (1.8 mmol) 2-Chloro-4,6-bis[N-(1-oxyl-2,2,6,6-tetramethylpiperidin-4-yl)butylamino]-s-triazine prepared under a) are dissolved in 15 ml cyclohexyl methylketone and 5 ml (147 mmol) of a 50% hydrogen peroxide solution is added. 30 mg CuCl are added at room temperature and the reaction mixture is stirred at room temperature for 48 h. 50 ml of ethyl acetate are added and the aqueous phase is separated. The organic phase is successively washed with 10% ascorbic acid solution, water, dil. sodium carbonate sol., dil. sodium chloride sol., and saturated sodium chloride sol. The organic phase is dried over sodium sulfate and finally dried to complete dryness under vacuum to yield a red oil. The product is purified by column chromatography (hexane/ethyl acetate 49:1) to provide 100 mg (8%) of pure product.
$^1$H-NMR (CDCl$_3$), δ (ppm): 0.94 (m, 6H), 1.15-1.40 (m, 39H), 1.49-1.61 (m, 10H), 1.62-1.82 (m, 8H), 2.05 (m, 4H), 3.32 (m, 4H), 3.61 (m, 2H), 5.00 (m, 2H).
$^{13}$C-NMR (CDCl$_3$), δ (ppm): 13.9, 14.0, 20.3, 20.5, 20.6, 20.8, 25.1, 25.9, 31.8, 31.9, 32.9, 34.6, 42.3, 42.5, 43.0, 43.5, 46.0, 46.1, 46.3, 60.2, 60.3, 81.9, 82.0, 164.6, 164.8, 168.9.

Example 4

Preparation of 1-Cyclohexyloxy-2,2,6,6-tetramethyl-piperidin-4-ol, compound 104

1.0 g 1-oxy-2,2,6,6-tetramethyl-piperidin-4-ol (Prostab 5198, commercial product of Ciba Specialty Chemicals Inc.) is dissolved in 7 ml cyclohexane carboxaldehyde and 5 ml of a 30% aqueous hydrogen peroxide solution are added. The emulsion is cooled to 10° C. and 50 mg CuCl are added. The reaction mixture is stirred over night at room temperature to give a greenish emulsion. The two phases are separated and the organic one is washed with 10% ascorbic acid solution, water, dil. sodium carbonate sol., dil. sodium chloride sol., and saturated sodium chloride sol. The organic phase is dried over sodium sulfate and finally evaporated to complete dryness under vacuum. The product is purified by column chromatography (hexane/ethyl acetate 15:1) to afford 1.1 g (71%) of pure product.
$^1$H-NMR (CDCl$_3$), δ (ppm): 1.20 (m, 18H), 1.51 (m, 3H), 1.81 (m, 4H), 2.06 (br s, 2H), 3.63 (m, 1H), 3.98 (m, 1H).
$^{13}$C-NMR (CDCl$_3$), δ (ppm): 21.0, 25.1, 25.9, 32.8, 34.8, 48.3, 48.8, 60.3, 62.9, 82.0.

Example 5

Preparation of 1-Methoxy-2,2,6,6-tetramethyl-piperidin-4-ol, compound 105

1.5 g 1-oxy-2,2,6,6-tetramethyl-piperidin-4-ol (8.71 mmol) (Prostab 5198, commercial product of Ciba Specialty Chemicals Inc.) are dissolved in a mixture of 20 ml ethanol and 15 ml 30% hydrogen peroxide. 50 mg CuCl are added and the mixture is kept at 50° C. for 18 h. After addition of 100 ml ethyl acetate, the organic phase is washed with 10% ascorbic acid and subsequently with water and brine. The organic phase is dried over sodium sulfate and evaporated to complete dryness to yield almost pure product. Yield: 540 mg (2.89 mmol, 33%); greenish solid.
$^1$H-NMR (CDCl$_3$), δ (ppm): 1.15 (t, 3 H), 1.23 (s, 3H), 1.48 (dd, 2H), 1.84 (dd, 2H), 3.63 (s, 3H), 3.97 (dddd, 1H).
$^{13}$C-NMR (CDCl$_3$), δ (ppm): 21.3, 33.6, 48.7, 60.4, 63.5, 65.9.

In analogy, the use of propanol leads to a 17% yield of 1-Ethoxy-2,2,6,6-tetramethyl-piperidin-4-ol, the use of 1-butanol leads to a 15% yield of 1-Propoxy-2,2,6,6-tetramethyl-piperidin-4-ol.

Example 6

Preparation of 1-Propoxy-2,2,6,6-tetramethyl-piperidin-4-ol, compound 106

2.0 g 1-oxy-2,2,6,6-tetramethyl-piperidin-4-ol (Prostab 5198, commercial product of Ciba Specialty Chemicals Inc.) are added to a mixture consisting of 5 ml butanal and 3 ml of a 30% aqueous hydrogen peroxide. 5 ml of toluene are added under stirring. The emulsion is cooled to 5° C. and 50 mg CuCl are added. The reaction mixture is stirred over night at room temperature to give a greenish emulsion. The two phases are separated and the organic one is washed with 10% ascorbic acid solution, water, dil. sodium carbonate sol., dil. sodium chloride sol., and saturated sodium chloride sol. The organic phase is dried over sodium sulfate and finally dried to complete dryness under vacuum to afford 1.9 g product.
$^1$H-NMR (CDCl$_3$), δ (ppm): 0.94 (t, 3 H), 1.14 (s, 3H), 1.21 (s, 3H), 1.47 (m, 4H), 1.80 (dd, 2H), 3.72 (dd, 2H), 3.97 (dddd, 1H).
$^{13}$C-NMR (CDCl$_3$), δ (ppm): 11.3, 21.4, 22.3, 33.6, 48.7, 60.4, 63.8, 78.8.

Example 7

Alternative method for the preparation of 1-Propoxy-2,2,6,6-tetramethyl-piperidin-4-ol, compound 106

1.8 g 2,2,6,6-tetramethyl-piperidin-4-ol (intermediate product of Ciba Specialty Chemicals Inc.) are suspended in 7 ml of toluene. 2.3 g of a 40% solution of peracetic acid in acetic acid are added at 0° C. and the reaction mixture is stirred at room temperature for 3 h. 4.2 ml butanal and 2.4 ml of a 30% aqueous hydrogen peroxide solution are added, followed by 50 mg CuCl after 15 min. The reaction mixture is stirred for 1.5 h at room temperature to give a greenish emulsion. The two phases are separated and the organic one is washed with 10% ascorbic acid solution, water, diluted sodium carbonate sol., diluted sodium chloride sol., and saturated sodium chloride sol. The organic phase is dried over sodium sulfate and finally evaporated to complete dryness under vacuum to afford 1.3 g product.

Example 8

Alternative method for the preparation of 1-Propoxy-2,2,6,6-tetramethyl-piperidin-4-ol, compound 106

1.8 g 2,2,6,6-tetramethyl-piperidin-4-ol (intermediate product of Ciba Specialty Chemicals Inc.) are suspended in 7 ml of toluene. 3.6 ml of a 30% aqueous hydrogen peroxide solution and 0.41 g acetic acid are added at 5° C. and the solution is stirred at room temperature over night. 4.2 ml butanal and, after 15 min., 50 mg CuCl are added. The reaction mixture is stirred for 18 h at room temperature. The two phases are separated and the organic one is washed with 0.05M hydrochloric acid, sodium bisulfite solution, water, diluted sodium hydroxide solution, water and finally saturated sodium chloride solution. The organic phase is dried over sodium sulfate and finally evaporated to complete dryness under vacuum to afford 0.38 g product.

Example 9

Preparation of 1-Propoxy-2,6-diethyl-4-hydroxy-2,3,6-trimethylpiperidine, compound 107

1.0 g 2,6-diethyl-4-hydroxy-2,3,6-trimethylpiperidine-1-N-oxyl are dissolved in 5 ml of toluene. 1.1 ml of a 30% aqueous hydrogen peroxide solution and 1.4 ml butanal are added, followed by 50 mg of CuCl after 10 min. The solution is stirred at room temperature for 1 d. The two phases are separated and the organic one is washed with 10% ascorbic acid solution, water, diluted sodium carbonate sol., diluted sodium chloride sol., and saturated sodium chloride sol. The organic phase is dried over sodium sulfate and finally evaporated to complete dryness under vacuum to afford 0.63 g product as a mixture of isomers.

Example 10

Preparation of 1-Octyloxy-2,2,6,6-tetramethyl-piperidin-4-ol, compound 108

20.0 g 1-oxy-2,2,6,6-tetramethyl-piperidin-4-ol (Prostab 5198, commercial product of Ciba Specialty Chemicals Inc.) are added to a mixture consisting of 50 ml toluene, 30 ml 30% aqueous hydrogen peroxide and 2 ml acetic acid. The emulsion is cooled to 15° C. and 50 mg CuCl are added. 50 ml of nonanal are added under vigorous stirring over 60 min. The reaction mixture is stirred for 12 h at room temperature to give a viscous, greenish mass. 100 ml tert. butylmethylether are added. The two phases are separated and the organic one is washed twice with 4 N NaOH, water, 10% ascorbic acid solution, water, and saturated sodium chloride sol. The organic phase is dried over sodium sulfate and finally dried to complete dryness under vacuum to afford 12.3 g product.

$^1$H-NMR (CDCl$_3$), δ (ppm): 0.87 (t, 3H), 1.15 (s, 3 H), 1.18 (s, 3H), 1.27 (2s, 6H), 1.14-1.42 (m, 10H), 1.49 (m, 2H), 1.79 (dd, 2H), 3.72 (t, 2H), 3.94 (dddd, 1H).

$^{13}$C-NMR (CDCl$_3$), δ (ppm): 13.9, 21.1, 22.6, 26.4, 28.7, 29.4, 29.7, 31.9, 33.3, 48.4, 59.9, 63.4, 77.1.

Example 11 bis(1-Octyloxy-2,2,6,6-tetramethyl-4-piperidyl) sebacate, compound 109

10.0 g Bis(1-oxyl-2,2,6,6-tetramethylpiperidin-4-yl) sebacate (Prostab 5415, commercial product of Ciba Specialty Chemicals Inc.) are dissolved in 50 ml toluene/acetic acid (1:1) and 2.5 g calcium chloride are added. 10 ml 50% aqueous hydrogen peroxide are added, followed by 20 ml nonanal and 0.2 g CuCl$_2$. The reaction mixture is stirred for 1 h at room temperature and afterwards for 10 h at 40° C. The mixture is pure into 100 ml 0.1 N NaOH and subsequently extracted with methylene chloride. The organic phase is washed twice with water and then with sat. sodium chloride solution and dried over sodium sulfate. The organic phase is removed in vacuo and the residue subjected to column chromatography on silica gel to afford 5.5 g of product.

The NMR data are identical with those published in the literature.

Example 11b bis(1-Octyloxy-2,2,6,6-tetramethyl-4-piperidyl) sebacate, compound 109

10.0 g Bis(1-oxyl-2,2,6,6-tetramethylpiperidin-4-yl) sebacate (Prostab 5415, commercial product of Ciba Specialty Chemicals Inc.) are dissolved in 40 ml toluene/tert-butanol (2:1) and 8 g 50% aqueous hydrogen peroxide are added, followed by 18 ml nonanal, 0.1 ml acetic acid and 0.15 g CuCl$_2$. The reaction mixture is stirred for 2 h at 25-25° C. and afterwards for 10 h at 40° C. The mixture is poured into 100 ml 0.1 N NaOH and subsequently extracted with methylene chloride. The organic phase is washed twice with water and then with sat. sodium chloride solution and dried over sodium sulfate. The organic phase is removed in vacuo and the residue subjected to column chromatography on silica gel to afford 5.4 g of product.

Example 12

Preparation of Phosphonic acid [1-[(1,1-dimethyl-ethyl)(1-phenylethoxy)amino]-2,2-dimethylpropyl]-diethyl ester, compound 110;

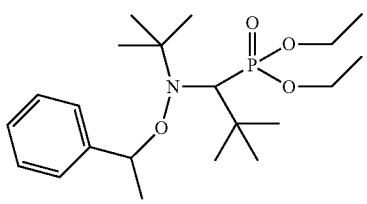 [SMILES: CCOP(=O)(OCC)C(N(OC(C)c1ccccc1)C(C)(C)C)C(C)(C)C]

1.0 g N-tert-Butyl-1-diethylphosphono-2,2-dimethylpropyl nitroxide is dissolved in 5 ml ethanol. 0.52 ml 30% aqueous hydrogen peroxide solution are added, followed by 0.68 g 2-phenylpropionaldehyde and 20 mg $CuCl_2$. The mixture is stirred at 30° C. for 12 h. The mixture is diluted with 50 ml methylene chloride and subsequently added to 40 ml 0.05 N NaOH. The organic phase is separated and successively washed with 1N NaOH, 10% aqueous ascorbic acid solution, water, 10% $Na_2EDTA$ aqueous solution and sat. sodium chloride solution and finally dried over sodium sulfate. The organic phase is removed in vacuo and the oily residue is subjected to column chromatography on silica gel (hexane/acetone) to afford 0.79 g (58%) pale yellow oil.

Example 13

2-Methyl-2-[N-[1-(diethoxyphosphinyl)-2,2-dimethylpropyl]aminoxy]propionic acid methyl ester, compound 111

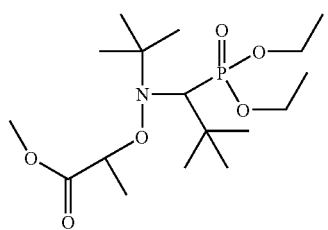 [SMILES: CCOP(=O)(OCC)C(N(OC(C)C(=O)OC)C(C)(C)C)C(C)(C)C]

The compound is prepared in analogy to example 12; yield 47% oil. Treatment with 0.5N NaOH in THF/water leads to 2-Methyl-2-[N-[1-(diethoxyphosphinyl)-2,2-dimethylpropyl]aminoxy]propionic acid,

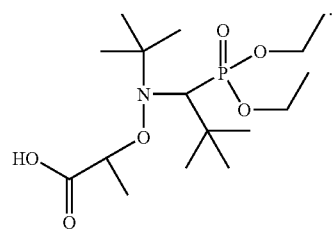 [SMILES: CCOP(=O)(OCC)C(N(OC(C)C(=O)O)C(C)(C)C)C(C)(C)C]

Example 14

1-[tert-Butyl-(1,1-dimethyl-2-oxo-propoxy)-amino]-2,2-dimethyl-propyl-phosphonic acid diethyl ester, compound 112

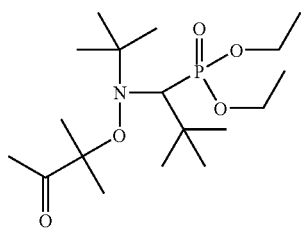 [SMILES: CCOP(=O)(OCC)C(N(OC(C)(C)C(C)=O)C(C)(C)C)C(C)(C)C]

The compound is prepared in analogy to example 12.

The following compounds in Table 1 and Table 2 have been prepared in analogy from the corresponding nitroxyl radical and the indicated ketone or aldehyde.

In Table 3 various solvents are given which can be used in the instant process. In Table 4 the use of various metal catalysts is demonstrated. In Table 5 reactions in water are outlined and in Table 6 the use of phase-transfer-catalysts is presented.

TABLE 1

| Example | Ketone | Product | Yield % |
|---|---|---|---|
| 15 | 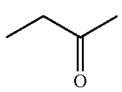 | 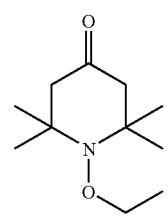 | 80 |
| 16 | | | 53 |

TABLE 1-continued

| Example | Ketone | Product | Yield % |
|---|---|---|---|
| 17 | pentan-3-one | 4-hydroxy-2,2,6,6-tetramethyl-1-ethoxypiperidine | 60 |
| 18 | 3-methylbutan-2-one | 4-hydroxy-2,2,6,6-tetramethyl-1-isopropoxypiperidine | 53 |
| 19 | pentan-2-one | 4-hydroxy-2,2,6,6-tetramethyl-1-propoxypiperidine | 60 |
| 20 | heptan-4-one | 4-hydroxy-2,2,6,6-tetramethyl-1-propoxypiperidine | 18 |
| 21 | 4-methylpentan-2-one | 4-hydroxy-2,2,6,6-tetramethyl-1-isobutoxypiperidine | 15 |
| 22 | 4-hydroxy-4-methylpentan-2-one | 4-hydroxy-2,2,6,6-tetramethyl-1-(2-hydroxy-2-methylpropoxy)piperidine | 10 |

TABLE 1-continued

| Example | Ketone | Product | Yield % |
|---|---|---|---|
| 23 | methoxyacetone | 2,2,6,6-tetramethyl-1-(methoxymethoxy)piperidin-4-ol | 92 |
| 24 | methyl pyruvate | methyl (4-hydroxy-2,2,6,6-tetramethylpiperidin-1-yl) carbonate | 43 |
| 25 | 4,4-dimethoxybutan-2-one | 1-(2,2-dimethoxyethoxy)-2,2,6,6-tetramethylpiperidin-4-ol | 40 |
| 26 | 1-cyclohexylethanone | 1-(cyclohexyloxy)-2,2,6,6-tetramethylpiperidin-4-ol | 37 |
| 27 | pentan-2-one | 1-butoxy-2,2,6,6-tetramethylpiperidin-4-ol | 23 |
| 28 | butan-2-one | 1-ethoxy-2,2,6,6-tetramethylpiperidin-4-one | 67 |

TABLE 1-continued

| Example | Ketone | Product | Yield % |
|---|---|---|---|
| 29 | pentan-2-one | 1-propoxy-2,2,6,6-tetramethylpiperidin-4-one | 81 |
| 30 | acetone | 1-methoxy-2,2,6,6-tetramethylpiperidin-4-one | 60 |
| 31 | 3,3-dimethylpentane-2,4-dione | 4-hydroxy-2,2,6,6-tetramethyl-1-(2-methyl-3-oxobutan-2-yloxy)piperidine | 45 |
| 32 | pentane-2,4-dione | 4-hydroxy-2,2,6,6-tetramethyl-1-(2-oxopropoxy)piperidine | 71 |
| 33 | 3-methylpentane-2,4-dione | 4-hydroxy-2,2,6,6-tetramethyl-1-(3-oxobutan-2-yloxy)piperidine | 5 |
| 34 | methyl 3-oxobutanoate | methyl 2-(4-hydroxy-2,2,6,6-tetramethylpiperidin-1-yloxy)acetate | 25 |

TABLE 1-continued

| Example | Ketone | Product | Yield % |
|---|---|---|---|
| 35 | methyl 4-oxopentanoate | TEMPO-O-CH2CH2C(O)OMe derivative | 9 |
| 36 | 3-acetyl-3-methyldihydrofuran-2(3H)-one | corresponding aminoxy lactone | 34 |
| 37 | 1-acetoxyacetone | corresponding aminoxy acetate | 59 |
| 38 | (methylthio)acetone | corresponding aminoxy sulfoxide | 8 |
| | | corresponding aminoxy sulfone | 23 |
| 39 | dimethyl (2-oxopropyl)phosphonate | corresponding aminoxy phosphonate | 28 |

TABLE 1-continued

| Example | Ketone | Product | Yield % |
|---|---|---|---|
| 40 | (1-(methylsulfonyl)propan-2-one) | (2,2,6,6-tetramethyl-4-hydroxypiperidin-1-yl methylsulfonylmethyl ether) | 39 |

TABLE 2

| Example | Aldehyde | Product | Yield % |
|---|---|---|---|
| 41 | 3-methylbutanal | 1-(isobutoxy)-2,2,6,6-tetramethylpiperidin-4-ol | 69 |
| 42 | 2-ethylbutanal | 1-(pentan-3-yloxy)-2,2,6,6-tetramethylpiperidin-4-ol | 71 |
| 43 | pivaldehyde | 1-(tert-butoxy)-2,2,6,6-tetramethylpiperidin-4-ol | 85 |
| 44 | octanal | 1-(octyloxy)-2,2,6,6-tetramethylpiperidin-4-ol | 37 |

TABLE 2-continued

| Example | Aldehyde | Product | Yield % |
|---|---|---|---|
| 45 | butyraldehyde | 4-hydroxy-1-propoxy-2,2,6,6-tetramethylpiperidine | 79 |
| 46 | cyclohexanecarboxaldehyde | 1-(cyclohexyloxy)-4-hydroxy-2,2,6,6-tetramethylpiperidine | 71 |
| 47 | undecanal | 4-hydroxy-1-(undecyloxy)-2,2,6,6-tetramethylpiperidine | 30 |
| 48 | 5-norbornene-2-carboxaldehyde | 4-hydroxy-1-(norbornenyloxy)-2,2,6,6-tetramethylpiperidine | 73 |
| 49 | 2,5-dimethyl-4-hexenal | 4-hydroxy-1-(2,5-dimethyl-4-hexenyloxy)-2,2,6,6-tetramethylpiperidine | 69 |
| 50 | pyruvaldehyde | 1-acetoxy-4-hydroxy-2,2,6,6-tetramethylpiperidine | 42 |

TABLE 2-continued

| Example | Aldehyde | Product | Yield % |
|---|---|---|---|
| 51 | pivaldehyde (tBu-CHO) | 4-cyano-1-(tert-butoxy)-2,2,6,6-tetramethylpiperidine | 68 |
| 52 | 2-phenylpropanal | 4-hydroxy-1-(1-phenylethoxy)-2,2,6,6-tetramethylpiperidine | 75 |
| 53 | diphenylacetaldehyde | 4-hydroxy-1-(diphenylmethoxy)-2,2,6,6-tetramethylpiperidine | 71 |
| 54 | phenylacetaldehyde | 4-hydroxy-1-(benzyloxy)-2,2,6,6-tetramethylpiperidine | 64 |
| 55 | butyraldehyde | 2,6-diethyl-2,3,6-trimethyl-1-propoxypiperidin-4-one | 66 |

TABLE 2-continued

| Example | Aldehyde | Product | Yield % |
|---|---|---|---|
| 56 | propanal | 2,2,6,6-tetramethyl-1-ethoxy-piperidin-4-one | 71 |
| 57 | butanal | 2,2,6,6-tetramethyl-1-propoxy-piperidin-4-one | 65 |
| 58 | butanal | 2,2,6,6-tetramethyl-1-propoxy-piperidin-4-one | 81 |
| 59 | acetaldehyde | 2,2,6,6-tetramethyl-1-methoxy-piperidin-4-one | 67 |
| 60 | heptanal | 2,2,6,6-tetramethyl-1-hexyloxy-piperidin-4-one | 64 |
| 61 | nonanal | 2,2,6,6-tetramethyl-1-octyloxy-piperidin-4-one | 43 |

TABLE 2-continued

| Example | Aldehyde | Product | Yield % |
|---|---|---|---|
| 62 | 2-phenylpropanal | TEMPO-derived 1-phenylethoxy piperidin-4-one | 65 |
| 63 | phenylacetaldehyde | TEMPO-derived benzyloxy piperidin-4-one | 51 |
| 64 | glutaraldehyde | bis(4-hydroxy-2,2,6,6-tetramethylpiperidin-1-yloxy)ethane | 25 |
|  |  | 4-hydroxy-TEMPO-O-CH₂CH₂-CHO | 33 |
|  |  | 4-hydroxy-TEMPO-O-CH₂CH₂-COOH | 7 |
| 65 | 2-methylpentanal | 4-hydroxy-2,2,6,6-tetramethyl-1-(pentan-2-yloxy)piperidine | 81 |

TABLE 2-continued

| Example | Aldehyde | Product | Yield % |
|---|---|---|---|
| 66 | 2-ethylhexanal | 1-(1-ethylpentyloxy)-2,2,6,6-tetramethylpiperidin-4-ol | 76 |
| 67 | pentanal | 1-butoxy-2,2,6,6-tetramethylpiperidin-4-one | 76 |
| 68 | hexanal | 1-pentyloxy-2,2,6,6-tetramethylpiperidin-4-one | 71 |
| 69 | octanal | 1-heptyloxy-2,2,6,6-tetramethylpiperidin-4-one | 57 |
| 70 | 2-ethylhexanal | 1-(1-ethylpentyloxy)-2,2,6,6-tetramethylpiperidin-4-one | 76 |

TABLE 2-continued

| Example | Aldehyde | Product | Yield % |
|---|---|---|---|
| 71 | 2-methylpentanal | TMP-N-O-CH(CH₃)CH₂CH₂CH₃ (2,2,6,6-tetramethyl-1-(pentan-2-yloxy)piperidin-4-one) | 78 |
| 72 | pivaldehyde | 1-(tert-butoxy)-2,2,6,6-tetramethylpiperidin-4-one | 83 |
| 73 | 3-methylbutanal | 1-(isobutoxy)-2,2,6,6-tetramethylpiperidin-4-one | 66 |
| 74 | norbornene-2-carbaldehyde | 1-(norbornenyloxy)-2,2,6,6-tetramethylpiperidin-4-one | 41 |
| 75 | glutaraldehyde | bis-TEMPO ethylene bis-ether product | 36 |
|  |  | 1-(3-oxopropoxy)-2,2,6,6-tetramethylpiperidin-4-one | 29 |

TABLE 2-continued
| Example | Aldehyde | Product | Yield % |
|---|---|---|---|
| | | 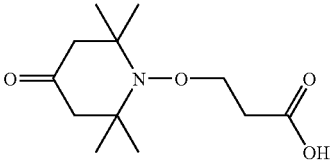 [SMILES: CC1(C)CC(=O)CC(C)(C)N1OCCC(=O)O] | 5 |
| 76 | 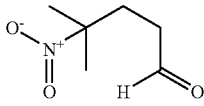 | 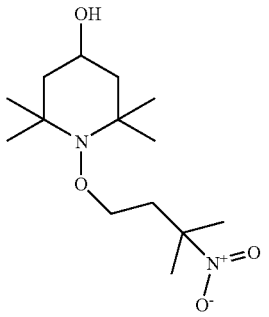 [SMILES: CC1(C)CC(O)CC(C)(C)N1OCCC(C)(C)[N+](=O)[O-]] | 17 |
| 77 | 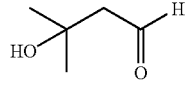 | 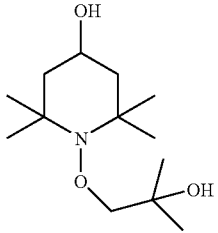 [SMILES: CC(C)(O)CON1C(C)(C)CC(O)CC1(C)C] | 34 |
| 78 |  | 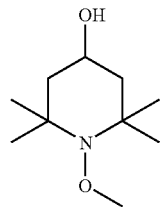 | 80 |
| 79 | 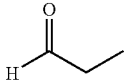 | 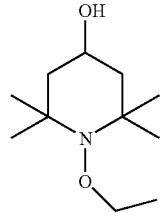 | 57 |
| 80 | 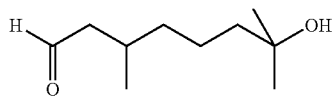 | 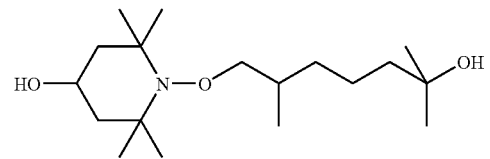 [SMILES: CC(CCCC(C)(C)O)CON1C(C)(C)CC(O)CC1(C)C] | 63 |

TABLE 2-continued

| Example | Aldehyde | Product | Yield % |
|---|---|---|---|
| 81 | isobutyraldehyde | 4-hydroxy-1-(isopropoxy)-2,2,6,6-tetramethylpiperidine | 92 |
| 82 | 3-oxopropanal (methylglyoxal-type) | N-(1-propoxy-2,2,6,6-tetramethylpiperidin-4-yl)acetamide | 66 |
| 83 | 2-phenylpropanal | 2,6-diethyl-2,3,6-trimethyl-1-(1-phenylethoxy)piperidin-4-one | 29 |

Example 84

Preparation of 1-Undecyloxy-2,2,6,6-tetramethyl-piperidin-4-ol, compound 108

10.0 g 1-oxy-2,2,6,6-tetramethyl-piperidin-4-ol (Prostab 5198, commercial product of Ciba Specialty Chemicals Inc.) are added to a mixture consisting of 40 ml water/ethanol (1:2) and 14.6 g dodecanal. 78 mg CuCl2 are added, and 5.1 g 50% aqueous hydrogen peroxide are added at RT. When a white precipitate starts to form, 40 ml of a mixture 30 ml ethanol and 10 ml toluene are added and the temperature is raised to 45° C. After 6 h another 2.5 g 50% H2O2e added and stirring is continued until TLC shows complete consumption of the starting material. 100 ml tert. butylmethylether are added. The two phases are separated and the organic one is washed twice with 1M NaOH, then with water, 10% ascorbic acid solution, water, and saturated sodium chloride sol. The organic phase is dried over sodium sulfate and finally dried to complete dryness under vacuum to afford 15.1 g product; tan oil. The product can be purified by means of column chromatography (hexane/acetone 49:1). Yield 9.9 g; colorless oil.

$^1$H-NMR (CDCl$_3$), δ (ppm): 0.86 (t, 3H), 1.14 (s, 3 H), 1.18 (s, 3H), 1.26 (2s, 6H), 1.14-1.52 (m, 20H), 1.79 (dd, 2H), 3.72 (t, 2H), 3.95 (dddd, 1H).

$^{13}$C-NMR (CDCl$_3$), δ (ppm): 14.0, 21.0, 22.7, 26.4, 28.7, 29.4, 29.6, 29.65, 29.7, 31.9, 33.3, 48.3, 59.9, 63.2, 77.0.

Bis(1-undecyloxy-2,2,6,6-tetramethyl-4-piperidyl) carbonate 2.5 g 1-undecyloxy-2,2,6,6-tetramethyl-piperidin-4-ol are dissolved in 12 ml 1,2-dichloroethane, 1.2 g pyridine are added, and the solution is cooled to 0° C. 1.1 g trichlorophosgene dissolved in 6 ml 1,2 dichloroethane are added over a period of 15 mins., keeping the temperature at ~10° C. The mixture is stirred at RT for 12 h. Afterwards, the solution is diluted with 70 ml methylene chloride, and 20 ml. saturated NH$_4$Cl-sol. are added. The aqueous phase is discarded and the organic phase is washed subsequently with 30 ml 1N HCl, 20 ml sat. Na$_2$CO$_3$-sol., water, brine. The organic phase is filtered over a buchner funnel filled with silica gel and eluted with methylene chloride. The solvent of the main fraction is removed in vacuo to yield a pale yellow oil; 1.2 g.

$^1$H-NMR (CDCl$_3$), δ (ppm): 0.88 (t, 3H), 1.18 (s, 3 H), 1.19 (s, 3H), 1.26 (2s, 6H), 1.14-1.42 (m, 18H), 1.51 (m, 2H), 1.62 (dd, 2H), 1.90 (dd, 2H), 3.71 (t, 2H), 4.84 (dddd, 1H).

$^{13}$C-NMR (CDCl$_3$), δ (ppm): 14.0, 21.0, 22.7, 26.4, 28.7, 29.4, 29.6, 29.65, 29.7, 31.9, 33.1, 44.0, 59.9, 63.2, 71.0, 77.1, 154.3.

Example 85

Alternative synthesis of bis(1-undecyloxy-2,2,6,6-tetramethyl-4-piperidyl)carbonate 24.9 g 1-oxy-2,2,6,6-tetramethyl-piperidin-4-ol (Prostab 5198, commercial product of Ciba Specialty Chemicals Inc.) are dissolved in 100 ml anhydrous methylene chloride, and the solution is cooled to 0° C. 14.7 g triethylamine are added in one portion, and 21.5 g triphosgene, dissolved in 75 ml methylene chloride, are added over a period of 2 h. The red solution is stirred at RT for 8 h. The reaction is quenched by the addition of 100 ml sat. $NH_4Cl$ sol. The aqueous phase is split off and the organic phase is washed subsequently with water, 10% $Na_2CO_3$-sol., and brine. The organic phase is dried over $Na_2SO_4$ and afterwards removed in vacuo to yield a light red solid; mp 179° C.

2 g of the obtained material is dissolved in 5 mol t-BuOH/toluene (4:1), 2.8 ml dodecanal, and 15 mg CuCl and 1.5 ml 30% $H_2O_2$. The mixture is stirred first at RT for the first hour and then at 40° C. for 12 h. After 5 h, another 1 ml of $H_2O_2$ is added. 30 ml of TBME are added and the organic phase is successively washed with water, 0.1 N NaOH, water, 10% EDTA-sol. and brine. The organic phase is dried over sodium sulfate and finally dried to complete dryness under vacuum to yield a brown oil. The product is purified by column chromatography (hexane/ethyl acetate 49:1) to provide 1.4 g product; slightly yellow oil.

Use of Different Solvents

Examplary reaction procedure for the preparation of 1-Propoxy-2,2,6,6-tetramethyl-piperidin-4-ol in toluene To a solution of 11.6 mmol of 1-oxy-2,2,6,6-tetramethyl-piperidin-4-ol (Prostab 5198, commercial product of Ciba Specialty Chemicals Inc.) in 5 ml toluene is added 50 mg CuI at RT. Under stirring, 17.4 mmol butyraldehyde are added, followed by 17.4 mmol of a 30% aqueous solution of $H_2O_2$ over a period of 25 min. The temperature is kept between 20-25° C. until the end of the reaction. Further addition of oxidant may be required in some cases. The organic phase is successively washed with 10% ascorbic acid solution, water, dil. sodium carbonate solution, dil. sodium chloride solution, and saturated sodium chloride solution. The organic phase is dried over sodium sulfate and finally evaporated to complete dryness under vacuum. Yield: 9.05 mmol, 78%

The following compounds in Table 3 have been prepared in analogy from the corresponding nitroxyl radical, butyraldehyde and the indicated solvent(s).

TABLE 3

| Solvent | Conversion of 1-oxy-2,2,6,6-tetramethyl-piperidin-4-ol (Prostab 5198) |
| --- | --- |
| Cyclohexane | 95 |
| Toluene/1-Hexene (2:1) | 90 |
| Chlorobenzene | 76 |
| tert-Butyl methyl ether | 63 |
| THF | 88 |
| Ethyl acetate | 62 |
| Methylene chloride | 64 |
| DMF | 80 |
| Ethanol | 75 |
| tert-Butanol | 76 |
| Water/tert-Butanol (1:8) | 78 |
| Water | 85 |
| Acetic acid | 89 |
| Water/Ethanol (1:1) | 79 |
| Ethylene glycol | 73 |
| Xylene | 69 |
| Amyl acetate | 61 |
| 1,4-Dioxane | 83 |
| 2-Ethoxyethanol | 75 |
| 1,1,1-Trichloroethane | 67 |
| 1-Butyl-3-methylimidazolium chloride | 77*) |

*)conversion after 6 h at 65-68° C.

Use of Different Catalysts

General Reaction Procedure:

To a solution of 11.6 mmol of Prostab 5198 in 5 ml toluene is added 3.5 mol % of the catalysts shown in table 4 at RT. Under stirring, 17.4 mmol butyraldehyde are added, followed by 17.4 mmol of a 30% aqueous solution of H2O2 over a period of 25 min. The temperature is kept between 20-25° C. until the end of the reaction. Further addition of oxidant may be required in some cases. The organic phase is successively washed with 10% ascorbic acid solution, water, dil. sodium carbonate sol., dil. sodium chloride sol., and saturated sodium chloride sol. The organic phase is dried over sodium sulfate and finally dried to complete dryness under vacuum.

TABLE 4

| Catalyst | Conversion of 1-oxy-2,2,6,6-tetramethyl-piperidin-4-ol, Prostab 5198 (toluene, after 22 h) | Conversion of 1-oxy-2,2,6,6-tetramethyl-piperidin-4-ol, Prostab 5198 (ethanol/water (2:1), after 22 h) |
| --- | --- | --- |
| CuCl | 86 | 95 |
| CuOAc | 5 | 64 |
| CuBr | 84 | 91 |
| $CuCl_2$ | 65 | 84 |
| $Cu(OAc)_2$ | 8 | 65 |
| $CuBr_2$ | 83 | 83 |
| $Cu(NO_3)_2$ | 5 | 80 |
| $CuSO_4$ | 12 | 93 |
| $Cu(acac)_2$ | 9 | 76 |
| Cu (100 mesh) | 3 | 81 |
| $Cu(OOCC_3H_7)_2$ | 67 | 76 |
| $Cu(gluconate)_2$ | 15 | 63 |
| Cu(CN) | 69 | 71 |
| $Cu(BF_4)_2$ | 35 | 68 |
| (Brass screw) | 7 | 69 |
| LiCl | 28 | |
| $MgCl_2$ | 29 | |
| $Al_2(SO_4)_3$ | 46 | |
| $CaCl_2$ | 58 | |
| $Sc(OTf)_3$ | 8 | |
| $Ti(OiPr)_4$ | 9 | |
| $MnCl_2$ | 83 | 45 |
| $Fe_2SO_4$ | 63 | 56 |
| $Co(OAc)_2$ | 4 | |
| $NiCl_2$ | 11 | |
| $ZrOCl_2$ | 72 | |
| $RuCl_3$ | 13 | |
| $PdCl_2$ | 61 | 66 |
| $InCl_3$ | 92 | |
| $La(OAc)_3$ | 17 | |
| $MeReO_3$ | 14 | |
| $BiCl_3$ | 46 | |
| $CoCl_2$ | 13 | |

TABLE 4-continued

| Catalyst | Conversion of 1-oxy-2,2,6,6-tetramethyl-piperidin-4-ol, Prostab 5198 (toluene, after 22 h) | Conversion of 1-oxy-2,2,6,6-tetramethyl-piperidin-4-ol, Prostab 5198 (ethanol/water (2:1), after 22 h) |
|---|---|---|
| $ZnCl_2$ | 78 | |
| $Fe_2O_3$ | 21 | 68 |

Reactions in Water as Solvent

Example A

Alternative method for the preparation of 1-Methoxy-2,2,6,6-tetramethyl-piperidin-4-ol 50 g 1-oxy-2,2,6,6-tetramethyl-piperidin-4-ol (290 mmol) (Prostab 5198, commercial product of Ciba Specialty Chemicals Inc.) are dissolved in 250 ml of water, and 17 g (290 mmol) sodium chloride (Fluka No. 71381) are added. 51.1 g (1.16 mol) acetaldehyde are added at once. 29.62 g 30% hydrogen peroxide (871 mmol) are added with stirring to the mixture in such a rate that the reaction temperature does not exceed 37° C. The mixture is then heated slowly to 90° C. and stirred there for further 2 h. The mixture is cooled to 25° C. with stirring, neutralized with sodium carbonate solution, and the peroxides destroyed with sodium bisulfite solution. The pH is adjusted to 11-12, and the crystals are filtered off and dried in vacuo at 80° C. Yield 32.79 g (60%).

The following catalysts, under varied conditions, give similar results in water:

TABLE 5

| Catalyst | Isolated yield | Remarks |
|---|---|---|
| CuCl | 48% | 3 days; max 45° |
| $Cu_2SO_4$ anhydrous | 54% | 65° |
| $Cu(OAc)_2 \cdot H_2O$ | 48% | 65° |
| $CaCl_2$ | 60% turnover | 65° |
| $ZnCl_2$ | 54% | 65° |
| $MnCl_2$ | 48% | 65° |
| Mg metal | >90% turnover | 60° |
| Al metal | >90% turnover | 60° |
| Fe metal | 90% turnover | 60° |
| Cu metal | >90% turnover | 60° |
| Zn metal | >90% turnover | 60° |
| Ag metal | 10% turnover | 60° |
| NaCl | 37% | 65° |
| LiCl | 35% | 65° |
| $CaCl_2 \cdot 6H_2O$ | 46% | 88° |
| $MgCl_2 \cdot 6H_2O$ | 39% | 97° |
| $AlCl_3 \cdot 6H_2O$ | 43% | 100° |
| $CuCl_2 \cdot 2H_2O$ | 58% | 90° |
| NaCl | 20% turnover | acetone replacing acetaldehyde |
| NaCl | 70.6% | NaCl/water/acetaldehyde mixed, then nitroxyl in water added at 25°; 96° |
| Halite (unpurified NaCl) | >75% turnover | 60-90° |
| No catalyst (blank) | 15% | 92° |

The reaction time is 3 days in all experiments

Example B

Alternative method for the preparation of 1-Ethoxy-2,2,6,6-tetramethyl-piperidin-4-ol 10 g 1-oxy-2,2,6,6-tetramethyl-piperidin-4-ol and 3.38 g sodium chloride are dissolved in water (50 ml). 17.1 ml propionaldehyde are added at once. The reaction mass is heated to 60°, and 17.8 ml 30% hydrogen peroxide slowly added with stirring at 60-70°. The mixture is stirred at 98° for further 2 h, cooled to 40°, sodium bisulfite solution added, and then the pH adjusted to 11-12 by adding sodium carbonate solution. The crystals are filtered off, washed with water, and dissolved in toluene. The solution is dried over sodium sulfate, and evaporated in vacuo. Yield 8.53 g (73%).

In Analogy to Example B

Example C

1-Isopropoxy-2,2,6,6-tetramethyl-piperidin-4-ol from isobutyraldehyde; yield 76%.

Example D

1-Cyclohexyloxy-2,2,6,6-tetramethyl-piperidin-4-ol from cyclohexanecarboxy-aldehyde; yield 23%.

Example E

Alternative method for the preparation of 1-Methoxy-2,2,6,6-tetramethyl-piperidin-4-one 10 g 1-Oxy-2,2,6,6-tetramethyl-piperidin-4-one are suspended with stirring in water (30 ml). 3.43 g sodium chloride in water (20 ml) are added, then 13.26 ml acetaldehyde are added at once. The mixture is warmed with stirring to 60°, then 18 ml 30% hydrogen peroxide is slowly added with stirring. The mixture is warmed to 90° and stirred for 2 h. The mixture is cooled, and the peroxides are destroyed with 10% sodium bisulfite solution (10 ml). The pH is adjusted to 11 with sodium carbonate solution. The mixture is extracted twice with toluene. The toluene phase is dried with sodium sulfate, and evaporated in vacuo. Yield 8.12 g (75%), liquid, crystallizes slowly.

In Analogy to Example E

Example E1

One-pot method for the preparation of 1-Methoxy-2,2,6,6-tetramethyl-piperidin-4-one The intermediate, 1-oxy-2,2,6,6-tetramethyl-piperidin-4-one, can be produced by reacting 2,2,6,6-tetramethyl-piperidin-4-one with 3 equivalents of hydrogen peroxide in excess water, with 10% sodium carbonate added, for 5 h at 50°. When the reaction is complete, the solution is slightly acidified with 2 N hydrochloric acid to pH 5, then 3 equivalents of acetaldehyde and one equivalent of sodium chloride are added, and two equivalents of 30% hydrogen peroxide are added slowly at 50°. The mixture is stirred at 90° for 2 h, and then cooled. The work-up, as above in example E, gives 62% of liquid product, crystallizes slowly.

Example E2

One-pot method for the preparation of 1-Methoxy-2,2,6,6-tetramethyl-piperidin-4-one The intermediate, 1-oxy-2,2,6,6-tetramethyl-piperidin-4-one, can be produced by reacting 2,2,6,6-tetramethyl-piperidin-4-one with 1.75 equivalents of hydrogen peroxide in 2M sodium chloride solution, with 1 mol % sodium tungstate added, for 12 h at 50°. When the reaction is complete, the solution is slightly acidified with 2 N hydrochloric acid to pH 5, then 3 equivalents of acetaldehyde and two equivalents of 30% hydrogen peroxide are added slowly at 50°. The mixture is stirred at 90° for 2 h, and then cooled. The work-up, as above in example E, gives 64% of liquid product, crystallizes slowly.

In Analogy to Example E

Example F

1-Ethoxy-2,2,6,6-tetramethyl-piperidin-4-one from propionaldehyde; yield: 78%, liquid, crystallizes slowly.

Example G

Method for the preparation of 1-Ethoxy-2,2,6,6-tetramethyl-piperidin-4-one

To a solution of 76.5 g 4-Oxo-2,2,6,6-tetramethylpiperidine-1-oxyl in 350 ml water and 20 ml ethanol are added 39 g propionaldehyde, 1.5 ml acetic acid and 0.65 g CuCl. 57 ml 30% hydrogen peroxide in water are added dropwise at RT over a period of 60 min. After 8 h another 10 ml of 30% $H_2O_2$ are added to drive the reaction to completion. After 12 h the reaction mixture is extracted twice with ethyl acetate. The organic phase is subsequently washed with sodium carbonate sol., 10% ascorbic acid solution, water and saturated sodium chloride sol. After drying over sodium sulfate, the solvent is removed under vacuum to afford 82 g of a blue oil. The compound is purified via distillation to afford 64.6 g product.

Example H

Preparation of 1-Butoxy-2,2,6,6-tetramethyl-piperidin-4-one 10 g 1-Oxy-2,2,6,6-tetramethyl-piperidin-4-one are suspended with stirring in water (50 ml). 3.45 g sodium chloride are added, then 10 g (12.3 ml) 1-pentanal (valeraldehyde) are added at once. The mixture is warmed with stirring to 60°, then 17.8 ml 30% hydrogen peroxide is slowly added with stirring. The mixture is warmed to 90° and stirred for 4 h. The mixture is cooled to 25° and extracted twice with dichloromethane. The organic phases are washed with water, dried with sodium sulfate, and evaporated in vacuo. The residue is chromatographed over silica gel with hexane/ethyl acetate 8:2 as eluent; yield: 26% of liquid, colorless product.

Example I

Preparation of 1-Pentoxy-2,2,6,6-tetramethyl-piperidin-4-one 10 g 1-Oxy-2,2,6,6-tetramethyl-piperidin-4-one are suspended with stirring in water (50 ml). 3.45 g sodium chloride are added, then 11.6 g (14.3 ml) 1-hexanal (capronaldehyde) are added at once. The mixture is warmed with stirring to 60°, then 17.8 ml 30% hydrogen peroxide is slowly added with stirring. The mixture is warmed to 90° and stirred for 4 h. The mixture is cooled to 25° and extracted twice with dichloromethane. The organic phases are washed with water, dried with sodium sulfate, and evaporated in vacuo. The residue is chromatographed over silica gel with hexane/ethyl acetate 8:2 as eluent; yield: 27% of liquid, colorless product.

Example J

Preparation of 1-Hexyloxy-2,2,6,6-tetramethyl-piperidin-4-one 10 g 1-Oxy-2,2,6,6-tetramethyl-piperidin-4-one are suspended with stirring in water (50 ml). 3.45 g sodium chloride are added, then 13.2 g (16.2 ml) 1-heptanal (oenanthal) are added at once. The mixture is warmed with stirring to 60°, then 17.8 ml 30% hydrogen peroxide is slowly added with stirring. The mixture is warmed to 90° and stirred for 4 h. The mixture is cooled to 25° and extracted twice with dichloromethane. The organic phases are washed with water, dried with sodium sulfate, and evaporated in vacuo. The residue is chromatographed over silica gel with hexane/ethyl acetate 8:2 as eluent; yield: 23% of liquid, colorless product.

Use of Phase Transfer Catalysts:

To a solution of 11.6 mmol of Prostab 5198 in 5 ml toluene is added 2.5 mol % of CuCl and 2.5 mol % of phase transfer catalyst at RT as indicated in Table 5. Under stirring, 17.4 mmol butyraldehyde are added, followed by 17.4 mmol of a 30% aqueous solution of H2O2 over a period of 25 min. The temperature is kept between 20-25° C. until the end of the reaction. Further addition of oxidant may be required in some cases. The organic phase is successively washed with 10% ascorbic acid solution, water, dil. sodium carbonate solution, dil. sodium chloride solution, and saturated sodium chloride solution. The organic phase is dried over sodium sulfate and finally dried to complete dryness under vacuum.

TABLE 6

| Phase transfer catalyst | Conversion of 1-oxy-2,2,6,6-tetramethyl-piperidin-4-ol, Prostab 5198 (after 8 h) |
|---|---|
| Bu$_4$NBr | 80 |
| C$_{16}$H$_{33}$Me$_3$NBr | 77 |
| MeOct$_3$NBr | 73 |
| 18-crown-6 | 78 |
| BnBu$_3$NBr | 82 |
| EtPh$_2$PBr | 78 |
| Polyethylene glycol 400 | 77 |
| Adogen ® 464 | 79 |
| Aliquat ® 336 | 75 |
| 1,4,8,11-Tetraazacyclotetradecane (Cyclam) | 76 |
| Tris(3,6-dioxaheptyl)amine | 72 |

The invention claimed is:

1. A process for the preparation of a sterically hindered nitroxyl ether which comprises reacting a corresponding sterically hindered nitroxyl radical with a carbonyl compound in the presence of a hydroperoxide and a metal catalyst, with the proviso that, if the sterically hindered nitroxyl radical is 2,2,6,6-tetramethylpiperidine-1-oxyl (TEMPO), the ketone is not acetone, where the carbonyl compound is an aldehyde, diketone, dialdehyde, oligoketone or oligoaldehyde and wherein the sterically hindered nitroxyl radical is selected from the group consisting of formulae (A)-(O)

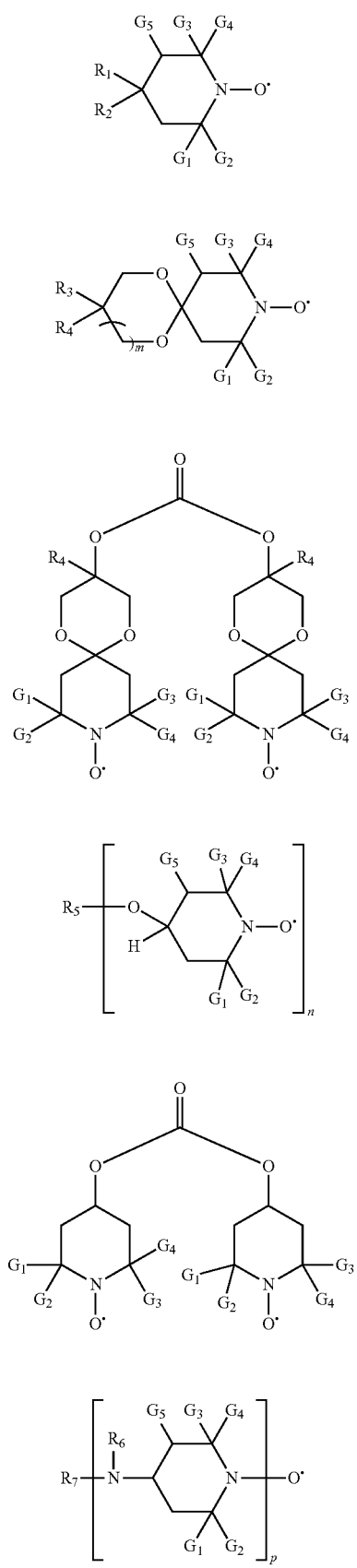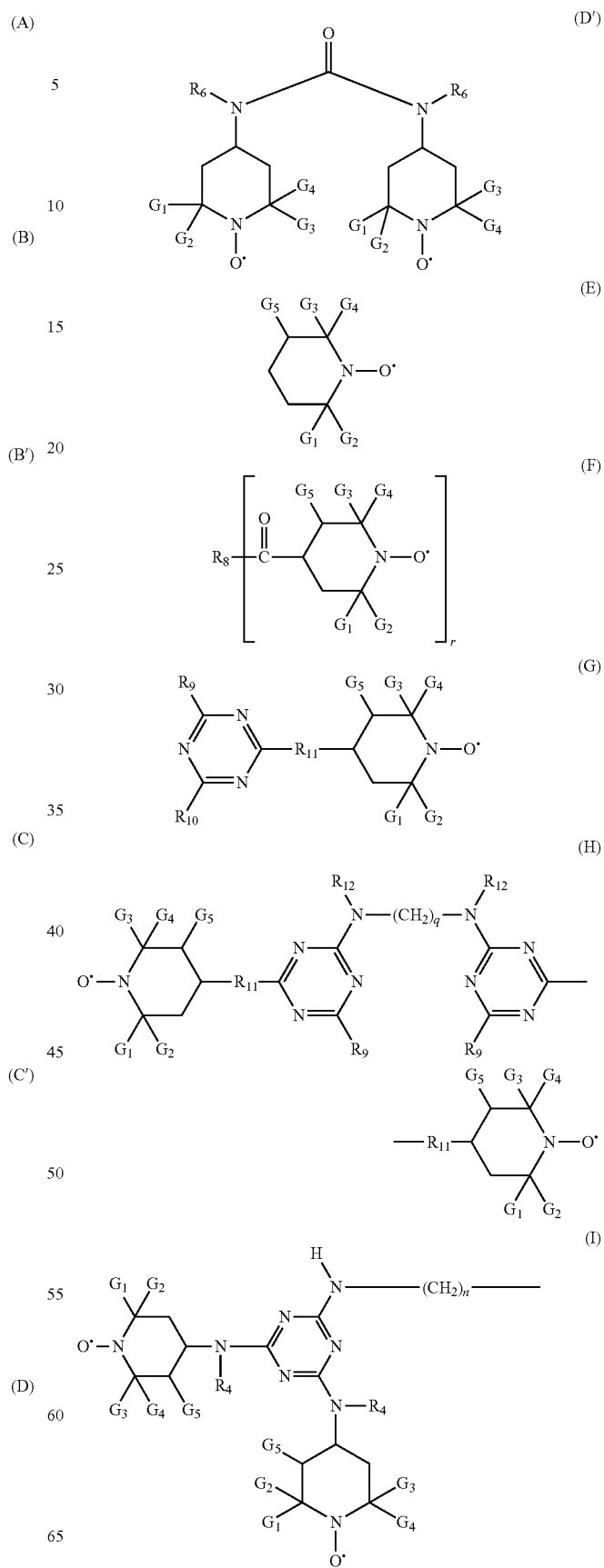

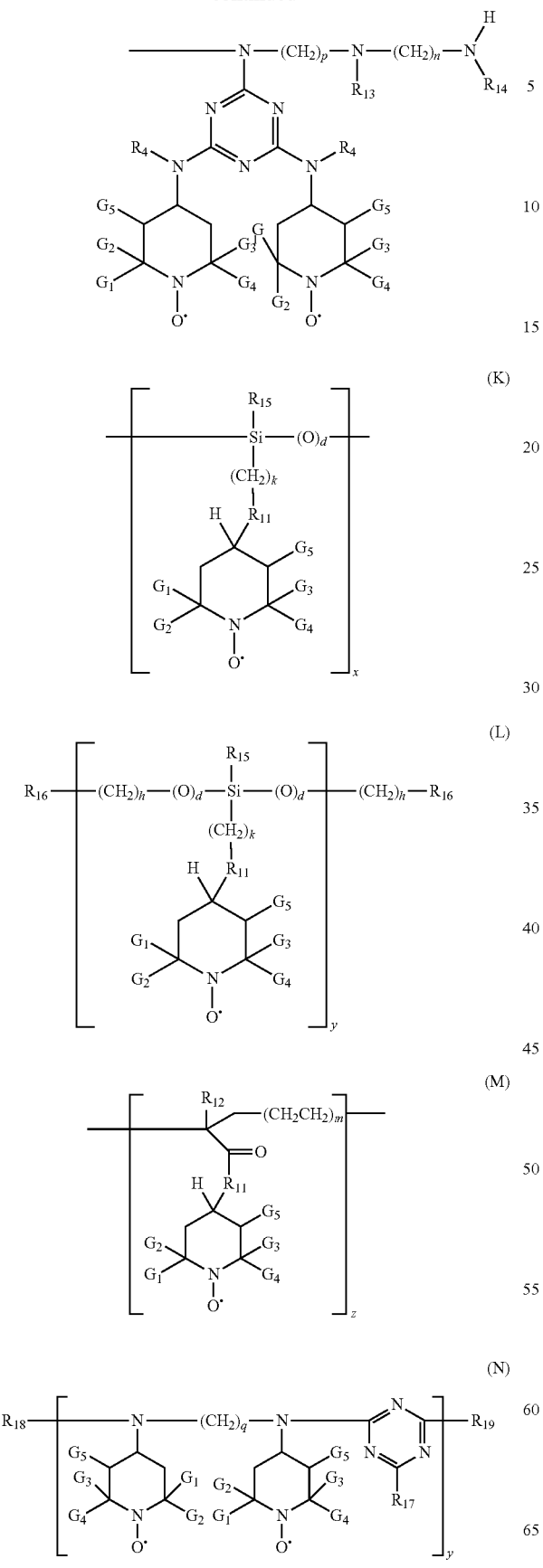

(O)

wherein
$G_1$, $G_2$, $G_3$, $G_4$ are independently $C_1$-$C_4$alkyl and $G_5$ is hydrogen or methyl;
$R_1$ is H and $R_2$ is OH;
m is 0 or 1;
$R_3$ is hydrogen, hydroxyl or hydroxymethyl, $C_1$-$C_{22}$alkanoyl, $C_1$-$C_{22}$alkoxycarbonyl or $C_1$-$C_{22}$alkanoyloxy;
$R_4$ is hydrogen, alkyl of 1 to 12 carbon atoms or alkenyl of 2 to 12 carbon atoms;
n is 1 to 4;
when n is 1,
$R_5$ is hydrogen, alkyl of 1 to 18 carbon atoms, alkoxycarbonylalkylenecarbonyl of 4 to 18 carbon atoms, alkenyl of 2 to 18 carbon atoms, glycidyl, 2,3-dihydroxypropyl, 2-hydroxy or 2-(hydroxymethyl) substituted alkyl of 3 to 12 carbon atoms which alkyl is interrupted by oxygen, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, or acyl radical of an aromatic acid containing 7 to 15 carbon atoms;
when n is 2,
$R_5$ is alkylene of 2 to 18 carbon atoms, a divalent acyl radical of an aliphatic or unsaturated aliphatic dicarboxylic or dicarbamic acid containing 2 to 18 carbon atoms, a divalent acyl radical of a cycloaliphatic dicarboxylic or dicarbamic acid containing 7 to 12 carbon atoms, or a divalent acyl radical of an aromatic dicarboxylic acid containing 8 to 15 carbon atoms;
when n is 3,
$R_5$ is a trivalent acyl radical of an aliphatic or unsaturated aliphatic tricarboxylic acid containing 6 to 18 carbon atoms, or a trivalent acyl radical of an aromatic tricarboxylic acid containing 9 to 15 carbon atoms;
when n is 4,
$R_5$ is a tetravalent acyl radical of an aliphatic or unsaturated aliphatic tetracarboxylic acid, or $R_5$ is a tetravalent acyl radical of an aromatic tetracarboxylic acid containing 10 to 18 carbon atoms;
p is 1 to 3;
$R_6$ is hydrogen alkyl of 1 to 18 carbon atoms or acyl of 2 to 6 carbon atoms or phenyl;
when p is 1,
$R_7$ is hydrogen, phenyl, alkyl of 1 to 18 carbon atoms, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, an acyl radical of an aromatic carboxylic acid containing 7 to 15 carbon atoms, or $R_6$ and $R_7$ together are —$(CH_2)_5CO$—, phthaloyl or a divalent acyl radical of maleic acid;
when p is 2,
$R_7$ is alkylene of 2 to 12 carbon atoms, a divalent acyl radical of an aliphatic or unsaturated aliphatic dicarboxylic or dicarbamic acid containing 2 to 18 carbon atoms, a divalent acyl radical of a cycloaliphatic dicarboxylic or dicarbamic acid containing 7 to 12 carbon atoms, or a divalent acyl radical of an aromatic dicarboxylic acid containing 8 to 15 carbon atoms;

when p is 3, $R_7$ is a trivalent acyl radical of an aliphatic or unsaturated aliphatic tricarboxylic acid containing 6 to 18 carbon atoms, or a trivalent acyl radical of an aromatic tricarboxylic acid containing 9 to 15 carbon atoms;

r is 1 to 4;

when r is 1, $R_8$ is alkoxy of 1 to 18 carbon atoms, alkenyloxy of 2 to 18 carbon atoms, —NHalkyl of 1 to 18 carbon atoms or —N(alkyl)$_2$ of 2 to 36 carbon atoms;

when r is 2, $R_8$ is alkylenedioxy of 2 to 18 carbon atoms, alkenylenedioxy of 2 to 18 carbon atoms, —NH-alkylene-NH— of 2 to 18 carbon atoms or —N(alkyl)-alkylene-N(alkyl)- of 2 to 18 carbon atoms, or $R_8$ is 4-methyl-1,3-phenylenediamino;

when r is 3, $R_8$ is a trivalent alkoxy radical of a saturated or unsaturated aliphatic triol containing 3 to 18 carbon atoms;

when r is 4, $R_8$ is a tetravalent alkoxy radical of a saturated or unsaturated aliphatic tetraol containing 4 to 18 carbon atoms;

$R_9$ and $R_{10}$ are independently chlorine alkoxy of 1 to 18 carbon atoms —O-$T_1$ amino substituted by 2-hydroxyethyl, —NH(alkyl) of 1 to 18 carbon atoms, —N(alkyl)$T_1$ with alkyl of 1 to 18 carbon atoms, or —N(alkyl)$_2$ of 2 to 36 carbon atoms;

$R_{11}$ is oxygen or $R_{11}$ is nitrogen substituted by either hydrogen, alkyl of 1 to 12 carbon atoms or $T_1$;

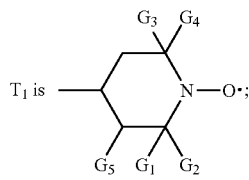

$R_{12}$ is hydrogen or methyl;

q is 2 to 8;

$R_{13}$ and $R_{14}$ are independently hydrogen or the group $T_2$;

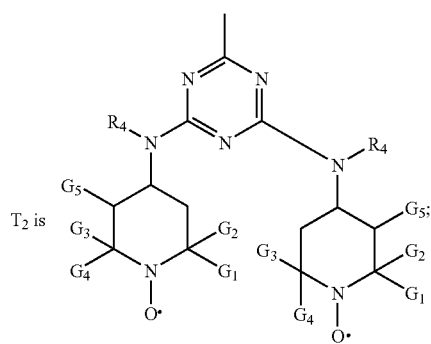

$R_{15}$ is hydrogen, phenyl, straight or branched alkyl of 1 to 12 carbon atoms, alkoxy of 1 to 12 carbon atoms, straight or branched alkyl of 1 to 4 carbon atoms substituted by phenyl, cycloalkyl of 5 to 8 carbon atoms, cycloalkenyl of 5 to 8 carbon atoms, alkenyl of 2 to 12 carbon atoms, glycidyl, allyloxy, straight or branched hydroxyalkyl of 1 to 4 carbon atoms, or silyl or silyloxy substituted three times independently by hydrogen, by phenyl, by alkyl of 1 to 4 carbon atoms or by alkoxy of 1 to 4 carbon atoms;

$R_{16}$ is hydrogen or silyl substituted three times independently by hydrogen, phenyl, by alkyl of 1 to 4 carbon atoms or by alkoxy of 1 to 4 carbon atoms;

d is 0 or 1;

h is 0 to 4;

k is 0 to 5;

x is 3 to 6;

y is 1 to 10;

z is an integer such that the compound has a molecular weight of 1000 to 4000 amu;

$R_{17}$ is morpholino, piperidino, 1-piperizinyl, alkylamino of 1 to 8 carbon atoms, —N(alkyl)$T_1$ with alkyl of 1 to 8 carbon atoms, or —N(alkyl)$_2$ of 2 to 16 carbon atoms;

$R_{18}$ is hydrogen acyl of 2 to 4 carbon atoms, carbamoyl substituted by alkyl of 1 to 4 carbon atoms, s-triazinyl substituted once by chlorine and once by $R_{17}$, or s-triazinyl substituted twice by $R_{17}$ with the condition that the two $R_{17}$ substituents may be different;

$R_{19}$ is chlorine, amino substituted by alkyl of 1 to 8 carbon atoms or by $T_1$, —N(alkyl)$T_1$ with alkyl of 1 to 8 carbon atoms, —N(alkyl)$_2$ of 2 to 16 carbon atoms, or the group $T_3$;

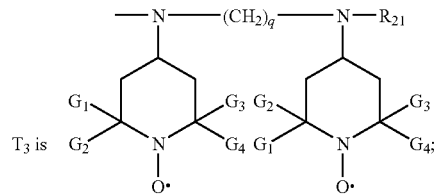

and $R_{21}$ is hydrogen, acyl of 2 to 4 carbon atoms, carbamoyl substituted by alkyl of 1 to 4 carbon atoms, s-triazinyl substituted twice by —N(alkyl)$_2$ of 2 to 16 carbon atoms or s-triazinyl substituted twice by —N(alkyl)$T_1$ with alkyl of 1 to 8 carbon atoms.

2. A process according to claim 1 wherein the carbonyl compound is a ketone, aldehyde, diketone or dialdehyde of formula (Ia) or (Ib)

(Ia)

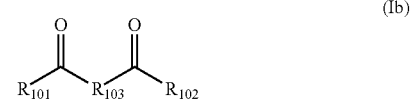

(Ib)

wherein $R_{101}$ and $R_{102}$ are independently hydrogen, straight or branched chain $C_1$-$C_{24}$alkyl, straight or branched chain $C_2$-$C_{18}$alkenyl, $C_2$-$C_{18}$alkinyl, $C_5$-$C_{12}$cycloalkyl, $C_5$-$C_{12}$cycloalkenyl, phenyl, naphthyl or $C_7$-$C_{15}$phenylalkyl; or said straight or branched chain $C_1$-$C_{24}$ alkyl, straight or branched chain $C_2$-$C_{24}$ alkenyl, $C_5$-$C_{12}$cycloalkyl, $C_5$-$C_{12}$cycloalkenyl or $C_2$-$C_{18}$alkinyl can be substituted by one or more -halogen, —OH, —$OR_{122}$, —$NH_2$, —$NHR_{122}$, —$N(R_{122})_2$, —$NHCOR_{122}$, —$NR_{122}COR_{122}$, —$OCOR_{122}$, —$COR_{122}$, —$SO_2R_{122}$, —$SR_{122}$, —$SOR_{122}$, —$P(OR_{122})_3$, —$P(O)(OR_{122})_2$ or $P(R_{122})_3$; or said straight or branched chain unsubstituted or substituted $C_1$-$C_{24}$ alkyl, straight or branched chain unsubstituted or substituted $C_2$-$C_{24}$ alkenyl, $C_5$-$C_{12}$ cycloalkyl, $C_5$-$C_{12}$cycloalkenyl or $C_2$-$C_{18}$ alkinyl can also be interrupted by one or more —O—, —NH— or —$NR_{122}$— groups or combinations thereof; or said phenyl, naphthyl or $C_7$-$C_{15}$phenylalkyl can also be substituted by one ore more halogen, —CN, —$CF_3$, —$NO_2$,

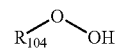

—$NHR_{122}$, —$N(R_{122})_2$, —OH, —$OR_{122}$ or —$COR_{122}$;
with the proviso that at least one of $R_{101}$ and $R_{102}$ is not hydrogen;
wherein * denotes the point of attachment;
$R_{122}$ is straight or branched chain $C_1$-$C_{18}$ alkyl, straight or branched chain $C_2$-$C_{18}$ alkenyl, $C_5$-$C_{10}$ cycloalkyl, phenyl, naphthyl or $C_7$-$C_{15}$ phenylalkyl; and
$R_{103}$ is a direct bond, $C_1$-$C_{24}$alkylene, $C_5$-$C_{12}$cycloalkylene, phenylene, $C_1$-$C_6$alkylene-phenylene, phenylene-$C_1$-$C_6$alkylene or $C_1$-$C_6$alkylene-phenylene-$C_1$-$C_6$alkylene.

3. A process according to claim 2 wherein the carbonyl compound is a ketone or aldehyde of formula (Ia)

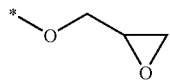

(Ia)

wherein $R_{101}$ and $R_{102}$ are hydrogen, straight or branched chain $C_1$-$C_{24}$alkyl, straight or branched chain $C_2$-$C_{18}$alkenyl, $C_2$-$C_{18}$alkyinyl, $C_5$-$C_{12}$cycloalkyl, $C_5$-$C_{12}$cycloalkenyl, phenyl, naphthyl or $C_7$-$C_{15}$phenylalkyl which may be unsubstituted or substituted by 1 to 3 OH groups.

4. A process according to claim 3 wherein $R_{101}$ and $R_{102}$ are hydrogen or straight or branched chain $C_1$-$C_{12}$alkyl, which alkyl may be unsubstituted or substituted by 1 OH group.

5. A process according to claim 1 wherein the hydroperoxide is of formula (II)

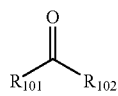

(II)

wherein
$R_{104}$ is hydrogen, $C_5$-$C_{12}$cycloalkyl, $C_1$-$C_{24}$alkyl, phenyl or phenyl substituted by 1-4 $C_1$-$C_4$alkyl groups.

6. A process according to claim 5 wherein the hydroperoxide is tert-butyl hydroperoxide, cumyl hydroperoxide or $H_2O_2$.

7. A process according to claim 1 wherein the metal catalyst is a salt or a complex of Ag, Mn, Fe, Cu, Zr, Na, Mg, Ca, Al, Pd, In, Bi or Ce in any oxidation state.

8. A process according to claim 7 wherein the metal catalyst is a salt or a complex of Fe, Cu, Mn, Na, Mg, Pd, In, Zr or Bi in any oxidation state.

9. A process according to claim 7 wherein the metal catalyst is a $Fe^{2+}$ or $Fe^{3+}$, a $Cu^+$ or $Cu^{2+}$, a $Na^+$ or a $Ca^{2+}$ salt.

10. A process according to claim 1 wherein $G_1$ and $G_3$ are ethyl and $G_2$, $G_4$ and $G_5$ are methyl or $G_1$ and $G_2$ are methyl, $G_3$ and $G_4$ are ethyl and $G_5$ is hydrogen or $G_1$, $G_2$, $G_3$ and $G_4$ are methyl and $G_5$ is hydrogen.

11. A process according to claim 1 wherein $G_1$, $G_2$, $G_3$ and $G_4$ are methyl and $G_5$ is hydrogen.

12. A process according to claim 1 wherein the sterically hindered nitroxyl radical is of formula (A), (B), (B'), (C), (C'), (G), (N) or (O).

13. A process according to claim 1 wherein the resulting sterically hindered nitroxyl ether contains a structural element of formula (XI)

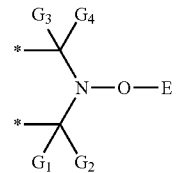

(XI)

wherein $G_1$, $G_2$, $G_3$ and $G_4$ are independently alkyl of 1 to 4 carbon atoms or $G_1$ and $G_2$ and/or $G_3$ and $G_4$ are together tetramethylene or pentamethylene and E is straight or branched chain $C_1$-$C_{24}$alkyl, straight or branched chain $C_2$-$C_{18}$alkenyl, $C_2$-$C_{18}$alkinyl, $C_5$-$C_{12}$cycloalkyl, $C_5$-$C_{12}$cycloalkenyl, phenyl, naphthyl or $C_7$-$C_{15}$phenylalkyl; or said straight or branched chain $C_1$-$C_{24}$ alkyl, straight or branched chain $C_2$-$C_{24}$alkenyl, $C_5$-$C_{12}$cycloalkyl, $C_5$-$C_{12}$cycloalkenyl or $C_2$-$C_{18}$alkinyl can be substituted by one or more -halogen, —OH, —$OR_{122}$, —$NH_2$, —$NHR_{122}$, —$N(R_{122})_2$, —$NHCOR_{122}$, —$NR_{122}COR_{122}$, —$OCOR_{122}$, —$COR_{122}$, —$SO_2R_{122}$, —$SR_{122}$, —$SOR_{122}$, —$P(OR_{122})_3$, —$P(O)(OR_{122})_2$ or $P(R_{122})_3$; or said straight or branched chain unsubstituted or substituted $C_1$-$C_{24}$ alkyl, straight or branched chain unsubstituted or substituted $C_2$-$C_{24}$alkenyl, $C_5$-$C_{12}$ cycloalkyl, $C_5$-$C_{12}$cycloalkenyl or $C_2$-$C_{18}$ alkinyl can also be interrupted by one or more —O—, —NH— or —$NR_{122}$— groups or combinations thereof; or said phenyl, naphthyl or $C_7$-$C_{15}$phenylalkyl can also be substituted by one ore more halogen, —CN, —$CF_3$, —$NO_2$,

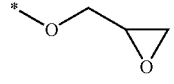 [SMILES: *OCC1CO1]

—$NHR_{122}$, —$N(R_{122})_2$, —OH, —$OR_{122}$ or —$COR_{122}$;
wherein * denotes the point of attachment; and
$R_{122}$ is straight or branched chain $C_1$-$C_{18}$ alkyl, straight or branched chain $C_2$-$C_{18}$ alkenyl, $C_5$-$C_{10}$ cycloalkyl, phenyl, naphthyl or $C_7$-$C_{15}$ phenylalkyl.

* * * * *